(12) United States Patent
Hamill et al.

(10) Patent No.: US 11,107,568 B2
(45) Date of Patent: Aug. 31, 2021

(54) VERSATILE DATA STRUCTURE FOR WORKOUT SESSION TEMPLATES AND WORKOUT SESSIONS

(71) Applicant: MYFITNESSPAL, INC., San Francisco, CA (US)

(72) Inventors: Ben Hamill, Austin, TX (US); Dory Glauberman, Austin, TX (US); James Lyke, Austin, TX (US); Jacob Peace, Austin, TX (US); Luis Valerio, Austin, TX (US); Carl Youngblood, Austin, TX (US)

(73) Assignee: MyFitnessPal, Inc., San Francisco, CA (US)

( * ) Notice: Subject to any disclaimer, the term of this patent is extended or adjusted under 35 U.S.C. 154(b) by 0 days.

(21) Appl. No.: 16/557,211

(22) Filed: Aug. 30, 2019

(65) Prior Publication Data
US 2021/0065869 A1    Mar. 4, 2021

(51) Int. Cl.
| | |
|---|---|
| *G06F 17/00* | (2019.01) |
| *G16H 20/30* | (2018.01) |
| *A61B 5/11* | (2006.01) |
| *G06F 3/0482* | (2013.01) |
| *A63B 24/00* | (2006.01) |

(52) U.S. Cl.
CPC ............ *G16H 20/30* (2018.01); *A61B 5/1118* (2013.01); *A63B 24/0062* (2013.01); *G06F 3/0482* (2013.01); *A63B 2024/0065* (2013.01); *A63B 2024/0068* (2013.01)

(58) Field of Classification Search
None
See application file for complete search history.

(56) References Cited

U.S. PATENT DOCUMENTS

| | | | |
|---|---|---|---|
| 2007/0072156 A1* | 3/2007 | Kaufman | G16H 20/60 434/236 |
| 2013/0106684 A1* | 5/2013 | Weast | A61B 5/6831 345/156 |
| 2014/0266731 A1* | 9/2014 | Malhotra | G06F 1/163 340/573.1 |
| 2015/0118667 A1* | 4/2015 | Andrew | G06Q 10/103 434/236 |
| 2016/0074707 A1* | 3/2016 | Thorpe | G09B 19/0076 434/127 |

(Continued)

OTHER PUBLICATIONS

Trainerize App Review by Sportuccino posted Oct. 14, 2016 on YouTube at https://www.youtube.com/watch?v=9yWzu5dq4bU last accessed by Examiner on Aug. 6, 2020, 8 pages. (Year: 2016).*

(Continued)

*Primary Examiner* — Paul A D'Agostino
(74) *Attorney, Agent, or Firm* — Maginot, Moore & Beck, LLP

(57) ABSTRACT

A fitness tracking system and methods collecting fitness data for a user during a workout session are disclosed. The fitness tracking system utilizes a versatile data structure for robustly representing complex workout session templates and recording fitness data associated with individual workout sessions. The versatile data structure enables detailed fitness data to be recorded in association with complex workout session templates in a manner that enables detailed analysis and a less cumbersome user experience.

20 Claims, 16 Drawing Sheets

(56) References Cited

U.S. PATENT DOCUMENTS

2018/0190375 A1* 7/2018 Chapela ............... A61B 5/6803
2020/0203012 A1* 6/2020 Kamath ............... A61B 5/7475

OTHER PUBLICATIONS

Trainerize Instructional Video posted May 22, 2016 on YouTube at https://www.youtube.com/watch?v=OkeTWED1iM last acced by Exmainer on Aug. 6, 2020, 12 pages. (Year: 2016).*
StrongApp, https://www.strong.app/, available as of Aug. 29, 2019.
Strong: Exercise Gym Log, 5x5, GooglePlayStore, https://play.google.com/store/apps/details?id=io.strongapp.strong&referrer=utm_source%3Dwebsite, available as of Aug. 29, 2019.
Strong Workout Tracker Gym Log, StrongApp AppleApp Store, https://apps.apple.com/us/app/strong-workout-tracker-pm-log/id464254577, available as of Aug. 29, 2019.

* cited by examiner

Jack's Workout Routine

Strength Training Days

| Push Day (Mon) 110 | Pull Day (Wed) 120 | Leg Day (Fri) 130 |
|---|---|---|
| Warm Up | Warm Up | Warm Up |
| • Stretch (5 min) | • Stretch (5 min) | • Stretch (5 min) |
| • Foam Rolling (5 min) | • Foam Rolling (5 min) | • Foam Rolling (5 min) |
| Workout | Workout | Workout |
| • 3x Circuits | • 3x Circuits | • Squats 3x4 (230 lb) |
|   o Bench Press x4 (170 lb) |   o Bicep Curls x4 (110 lb) | • Deadlifts 3x3 (270 lb) |
|   o Shoulder Press x5 (90 lb) |   o Lat Pulldowns x8 (90 lb) | • Leg Curls 3x8 (150 lb) |
| • Tricep Dips 3x12 (BW) |   o Bent-Over Rows x10 (60 lb) | Cool Down |
| Cool Down | Cool Down | • Walk (5 min) |
| • Walk (5 min) | • Walk (5 min) | |

Cardio Days

Running Intervals 140
(Tues/Thurs)

Warm Up
• Walk (5 min)
Workout
• Run (5 min)
• Walk (3 min)
• Run (8 min)
• Walk (3 min)
• Run (5 min)
Cool Down
• Walk (5 min)
• Stretch (5 min)

FIG. 3

VERSATILE DATA STRUCTURE FOR WORKOUT SESSION TEMPLATES AND WORKOUT SESSIONS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The device and method disclosed in this document relates fitness tracking systems and, more particularly, to a versatile data structure for workout session templates and workout sessions.

BACKGROUND

Smartphone applications and dedicated activity tracking devices are increasingly utilized by individuals interested in tracking metrics related to their personal health and fitness activity. These smartphone applications and dedicated activity tracking devices are easy to use for popular fitness activities, such as running, walking, or cycling, which are generally performed continuously for a period of time. The performance of the user during the fitness activity can generally be captured and evaluated with in straight forward manner, without complex user input. For example, during a run, performance metrics such as heart rate over time, total steps, total distance, and pace can easily be captured with minimal or no user inputs using suitable sensors, such as heart rate monitors, accelerometers, global positioning systems ("GPS"), as well as various other motion and biometric sensors.

However, many popular fitness activities, such as strength training and circuit training, generally involve sequences of diverse exercises, each of which have different metrics for evaluating performance of the user. Additionally, fitness activities such as interval training, involve alternating sequences of higher intensity activity intervals and lower intensity relief intervals or rest periods, often having a complex sequence of time durations for each interval, and sometimes also including a diverse set of exercises. Accordingly, robust and automated tracking of what exercises were performed and respective performance metrics for each exercise is significantly more challenging than for continuously performed fitness activities. As a result, if a user wants to document a fitness activity thoroughly, the user often needs to manually enter which exercises were performed, start and stop times for each exercise, and any performance metrics that were not captured automatically (e.g., in the case of strength training, a number of reps or a weight used). Alternatively, the user can simply document a fitness activity as if it were a continuously performed fitness activity, with a generic label such "weight lifting" or "high-intensity interval training." In view of the foregoing, it would be advantageous to provide a method and system for robustly recording complex workout sessions, without the need for complex and time consuming data entry by the user. It would also be advantageous if as much of the data entry is automated as possible, without loss of accuracy or robustness.

SUMMARY

In accordance with one exemplary embodiment of the disclosures, a method of collecting fitness data for a user during a workout session is disclosed. The method comprises storing, in a memory, a first data structure defining a workout session template formed by a first plurality of exercises. The first data structure has a first tree structure that depends upon and represents an organization of the first plurality of exercises in the workout session template. The method further comprises presenting, with a display screen, a graphical depiction of the workout session template to the user in response to receiving a request from the user to begin a workout. The method further comprises receiving, with a user interface, first inputs defining at least one change to the first data structure. The method further comprises generating, with the processor, a second data structure defining the workout session formed by a second plurality of exercises. The second data structure has a second tree structure that depends upon and represents an organization of the second plurality of exercises in the workout session. The second data structure is derived from and stores data of the first data structure and representing the change to the first data structure. The method further comprises storing, in the memory, the second data structure Pursuant to another exemplary embodiment of the disclosures, a further method of collecting fitness data for a user during a workout session is disclosed. The method comprises storing, in a memory, a plurality of first data structures each defining a respective workout session template formed by a respective first plurality of exercises. Each data structure in the plurality of first data structures has a respective first tree structure that depends upon and represents an organization of the respective first plurality of exercises in the respective workout session template. The method further comprises presenting, with a display screen, a list of the respective workout session templates defined in the plurality of first data structures. The method further comprises presenting, with a display screen, a graphical depiction of a first workout session template to the user in response to receiving a selection of the first workout session template from the list of templates. The method further comprises receiving, with a user interface, inputs defining an actual value for at least one performance metric for at least one exercise in the respective first plurality of exercises that form the first workout session template. The method further comprises generating, with the processor, a second data structure defining the workout session formed by a second plurality of exercises. The second data structure has a second tree structure that depends upon and represents an organization of the second plurality of exercises in the workout session. The second data structure is derived from and stores data of the respective first data structure that defines the first workout session template. The second tree structure stores the actual value for the at least one performance metric for the at least one exercise. The method further comprises storing, in the memory, the second data structure.

In accordance with yet another exemplary embodiment, an electronic device for collecting fitness data for a user during a workout session is disclosed. The electronic device comprises a display screen configured to display a graphical user interface to a user. The electronic device further comprises a user interface configured to receive inputs from the user. The electronic device further comprises a memory configured to store a first data structure defining a workout session template formed by a first plurality of exercises. The first data structure has a first tree structure that depends upon and represents an organization of the first plurality of exercises in the workout session template. The electronic device further comprises a processor operably connected to the display screen, the user interface, and the memory. The processor is configured execute program instructions to operate the display screen to present a graphical depiction of the workout session template to the user in response to receiving a request from the user to begin a workout. The processor is configured execute program instructions to operate the user interface to receive first inputs defining at least one change to the first data structure, the at least one change to the first data structure including at least one of (i) an actual value for at least one performance metric for at least one exercise in the first plurality of exercises, (ii) a change to the exercises in the first plurality of exercises, and (iii) a change to the organization of the first plurality of exercises in the workout session template. The processor is configured execute program instructions to generate a second data structure defining the workout session formed by a second plurality of exercises. The second data structure has a second tree structure that depends upon and represents an organization of the second plurality of exercises in the workout session. The second data structure is derived from and stores data of the first data structure and representing the change to the first data structure. The processor is configured execute program instructions to operate the memory store the second data structure.

These and other aspects of the disclosure shall become apparent when considered in light of the disclosure provided herein.

BRIEF DESCRIPTION OF THE DRAWINGS

The foregoing aspects and other features of a fitness tracking system are explained in the following description, taken in connection with the accompanying drawings.

FIG. 3 shows an exemplary set of workout session templates for a fictitious user.

All Figures ©Under Armour, Inc. 2019. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Fitness Tracking System

Figure 1:
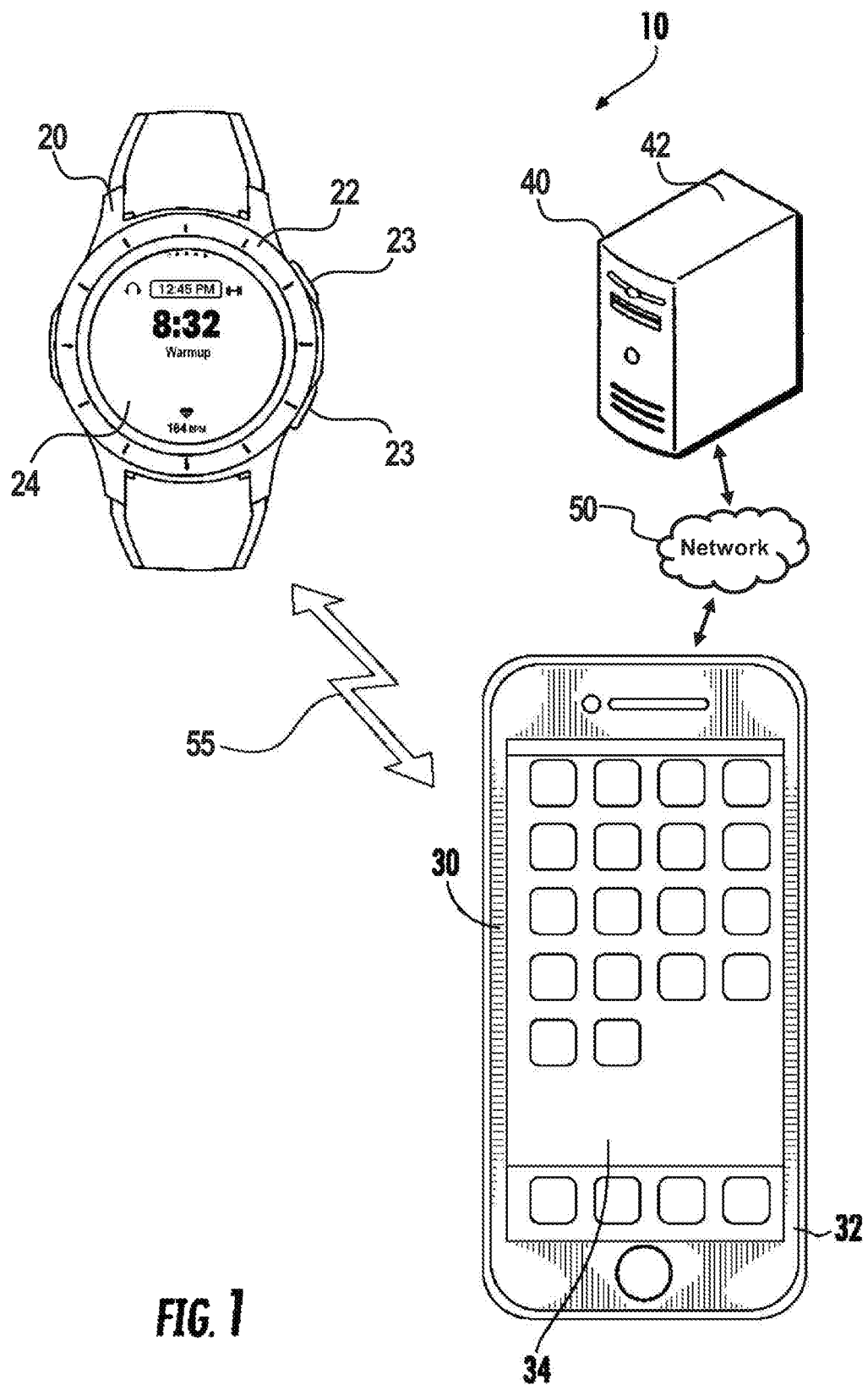
FIG. 1 is a diagrammatic view showing an exemplary embodiment of a fitness tracking system including an activity tracking device, a personal electronic device, and a system server.
Figure 2:
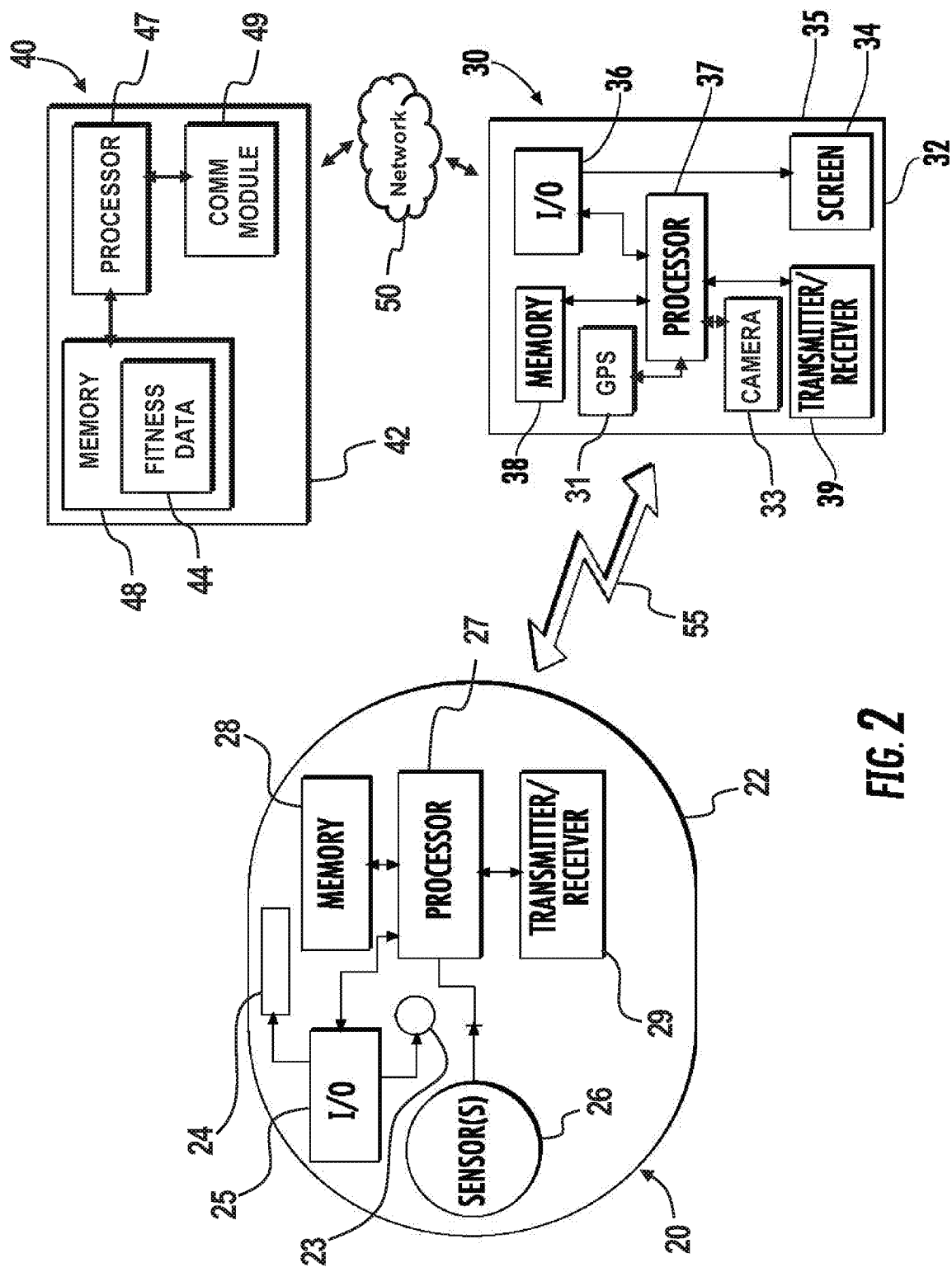
FIG. 2 is a block diagram of exemplary electronic components in the activity tracking device, the personal electronic device, and the system server of the fitness tracking system of FIG. 1.

With reference to FIGS. 1-2, an exemplary embodiment of a fitness tracking system 10 for recording fitness data during an activity or workout is disclosed (which may also be referred to herein as the "health tracking system" or the "activity tracking system"). As will be discussed in greater detail elsewhere herein, the fitness tracking system 10 utilizes a versatile data structure for robustly representing complex workout session templates and recording fitness data associated with individual workout sessions. The versatile data structure improves upon conventional fitness tracking systems by enabling detailed fitness data to be recorded in association with complex workout session templates in a manner that enables detailed analysis and coaching, with a less cumbersome user experience.

In the illustrated embodiment, the fitness tracking system 10 includes at least one personal electronic device 30 and a remote system server 40 in communication with at least the personal electronic device 30 via a network 50, such as the Internet. In some embodiments, the fitness tracking system 10 further includes at least one activity tracking device 20 in communication with at least the personal electronic device 30 and/or the server 40.

The personal electronic device 30, shown in the form of a smartphone, is as user device designed to receive fitness data, such as by enabling a user to input the fitness data, process the fitness data, and display it to the user in a format that summarizes a user's performance during an activity or workout and/or at some time thereafter. The term "fitness data" as used herein refers to data relating to a user's fitness and performance during an activity or workout, but also to data regarding the user's health and general well-being outside of the activity or workout and may also be referred to herein as "fitness information" or "fitness parameters." Fitness data may be in a raw measured form or in a processed form. Fitness data may be entered manually by the user via the personal electronic device 30 and/or the activity tracking device 20, but also may be automatically measured, sensed, or collected by the personal electronic device 30 and/or the activity tracking device 20. Fitness data may include activity data and physiological data. The term "activity data" as used herein is a subset of fitness data, and refers to data related to physical activity (i.e., movement or lack thereof) of the user. Examples of activity data include exercise weight/resistance data, exercise repetition data, time data (e.g., start times, stop times, durations), body motion/acceleration data, step data, stride length data, stride cadence data, distance traversal data, pace/speed data, altitude data, environmental/positional data (such as that provided by a GPS receiver), and/or any of various other types of personal activity metrics that may be relevant the user's physical activity for a given period of time. The term "physiological data" as used herein is a subset of fitness data, and refers to data related to the physiological status and health of the user. Examples of physiological data include age, gender, height, body weight, body fat, heart rate, aspiration rate, blood oxygenation, blood glucose, hydration, caloric expenditure, $VO_2$ max, or any of various other types of physiological metrics that may be relevant the user's physiological health for a given period of time. Fitness data may also include information related to the user's health and fitness goals, which may take the form of a target value for any of the health and fitness parameter's discussed above.

The remote system server 40 comprises a computing device or data processing system configured for storing and processing fitness data. The personal electronic device 30 and/or activity tracking device 20 may communicate fitness data to the system server 40 via the network 50 for processing and/or storage, thereby decreasing the processing and/or storage capacity required at either user device (e.g., the personal electronic device 30 or activity tracking device 20). In at least one embodiment, the remote system server 40 maintains a database of fitness data received from the personal electronic device 30 and/or the activity tracking device 20, as well as fitness data received from further personal electronic devices and/or activity tracking devices associated with a plurality of other users.

The activity tracking device 20 is a user device configured to measure one or more health and fitness parameters of a user during an activity or workout and provide fitness data regarding the activity or workout to the personal electronic device 30. In many embodiments, the activity tracking device 20 is designed and dimensioned to be worn on or carried by the body of a user. In another embodiment, the personal electronic device 30 may further comprise an activity tracking device 20. In the illustrated embodiment, the activity tracking device 20 is in the form of a so-called "smart" watch which is worn on the user's wrist. Any fitness data measured, sensed, or otherwise collected by the activity tracking device 20 is automatically delivered to the personal electronic device 30 and/or the system server 40. As represented by the arrow 55 in FIGS. 1 and 2, the activity tracking device 20 is configured to transmit a wireless signal representative of the fitness data collected or obtained thereat to the personal electronic device 30. In other embodiments, a wired connection may be utilized for communication of fitness data between the personal electronic device 30 and the activity tracking device 20.

It should be appreciated that, depending on the level of sophistication of the activity tracking device 20, the activity tracking device 20 may perform many of the same functions as the personal electronic device 30. In some embodiments, the activity tracking device 20 may have companion software which operates in conjunction with software of the personal electronic device 30 to enable a user to input fitness data, process the fitness data, and display it to the user in a format that summarizes a user's performance during an activity or workout. Likewise, the personal electronic device 30 may perform functions of the activity tracking device 20, such as automatically measuring one or more health and fitness parameters of a user during an activity or workout. In this way, features described herein with respect to the activity tracking device 20 and the personal electronic device 30 should be considered applicable to either device, and the devices 20, 30 may work in concert with one other to perform any client-side functions.

Personal Electronic Device

With continued reference to FIGS. 1-2, the personal electronic device 30 (also referred to herein as an "electronic display device" or a "health tracking device") is a computing device, such as a smartphone. However, while a smartphone has been shown as the personal electronic device 30 in FIG. 1, it will be appreciated that the personal electronic device 30 may alternatively comprise any number of devices. For example, the personal electronic device 30 may be any type of portable or other personal electronic device such as a watch, tablet computer, laptop computer, and/or any of various other mobile computing devices. Alternatively, the personal electronic device 30 may be a standalone device, such as a desktop PC, and/or smart television. As will be recognized by those of ordinary skill in the art, the components of the personal electronic device 30 may vary depending on the type of display device used. Such alternative display devices may include much (but not necessarily all) of the same functionality and components as the personal electronic device 30 shown in FIGS. 1 and 2, as well as additional functionality or components necessary for proper functioning thereof (not shown).

In the illustrated embodiment of FIG. 2, the personal electronic device 30 includes an input/output (I/O) interface 36, a processor 37, a memory 38, and a transmitter/receiver 39. Additionally, the personal electronic device 30 generally includes a protective outer shell or housing 32 designed to retain and protect the electronic components positioned within the housing 32. The housing 32 may comprise any number of shapes, configurations, and/or materials, the description herein being merely exemplary. The personal electronic device 30 also includes a battery or other power source (not shown) configured to power the electronic components within the personal electronic device 30.

The I/O interface 36 of the personal electronic device 30 includes software and hardware configured to facilitate communications with any user interfaces or other input/output devices of the personal electronic device 30. The user interfaces at least include a display screen 34 configured to visually display graphics, text, and other data to the user. The user interfaces may also include a microphone and/or speakers to facilitate audio communications with the user and/or verbal entry of commands to the device 30. In at least one embodiment, the display screen 34 is a touch screen display that allows the user to see data presented on the display screen 34 and input data into the personal electronic device 30 via a virtual keyboard or other interface on the touch screen. However, the user interfaces may include other means for receiving user input, such as a physical keyboard and other tactile buttons, switches, and the like.

The processor 37 of the personal electronic device 30 may be any of various processors as will be recognized by those of ordinary skill in the art. The processor 37 is operably connected to the I/O interface 36, the memory 38, and the transmitter/receiver 39, and is configured to deliver data to and/or receive data from each of these components. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 38 is configured to store data and program instructions that, when executed by the processor, enable the personal electronic device 30 to perform various operations described herein. The data may be, for example, fitness data as discussed above, which may be related to the activities, workouts, health and fitness profile, etc. of the user, along with other operational data that may be ancillary to the basic operation of the personal electronic device 30 and any applications retained on the personal electronic device 30. The instructions stored at the memory 38 generally include firmware, an operating system, and/or other software for execution by the processor 37. In at least one embodiment, the instructions stored in the memory 38 include a client-side activity tracking application, discussed in greater detail below, which is executed by the processor 37 to process fitness data and present the fitness data in a graphical format on the display screen 34. The memory 38 may be of any type of device capable of storing information accessible by the processor, such as a memory card, ROM, RAM, write-capable memories, read-only memories, hard drives, discs, flash memory, or any of various other computer-readable medium serving as data storage devices, as will be recognized by those of ordinary skill in the art.

The transmitter/receiver 39 is, in one embodiment, an RF transmitter and receiver configured to transmit and receive communications signals using a wireless communications technology, such as Wi-Fi or Bluetooth®, using any of various communications protocols, such as TCP/IP. Such transmitter/receivers are well known and will be recognized by those of ordinary skill in the art. The transmitter/receiver 39 is at least configured to communicate with the system server 40 via the network 50 and configured to communicate with a transmitter/receiver 29 of the activity tracking device 20. In at least one embodiment, the transmitter/receiver 39 is configured to allow the personal electronic device 30 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

As mentioned above, in some embodiments, the personal electronic device 30 may automatically collect certain fitness data independent of the dedicated activity tracking devices 20. Particularly, in at least one embodiment, the personal electronic device 30 includes a GPS receiver 31 configured to record a global position of the user during an activity or workout. Additionally, in some embodiments, the personal electronic device 30 also includes additional sensors, such as a 3-axis accelerometer, altimeter, etc. (not shown), configured to record fitness data during an activity or workout.

In at least one embodiment, the personal electronic device 30 includes a camera 33 having at least one photo-sensitive element configured to capture an image and/or video of the surroundings. The processor 37 is configured to operate the camera 33 to capture the image and/or video, to receive the image and/or video from the camera 33, and to store the image and/or video in the memory 38. A user may initiate capture of the image and/or video by pressing virtual buttons (not shown) on the display screen 34 or by pressing physical buttons (not shown) of the personal electronic device 30. Alternatively, the image capture may be automatically initiated by the device 30 such as upon determination that a particular activity is occurring; thereafter a user may be required to affirmatively approve the actual capture of images.

Activity Tracking Device

With continued reference to FIGS. 1-2, the activity tracking device 20 (which may also be referred to herein as "health tracking devices" or a "sensor devices") may be provided in any of various forms. In the embodiment shown in FIG. 1, the activity tracking device 20 is provided as a "smart" watch that the user straps to his or her wrist. It will be recognized that in other embodiments, further activity tracking devices may be provided in any of various different configurations to be worn on any of various locations on the body of the user, such as via a module that clips on to clothing, is worn on a chest strap, fits in a pocket of the user, and/or is incorporated into a garment such as a shoe, or a hat, and/or other accessories such as glasses or belts. Additional or alternative examples of activity tracking devices include those sold under the trademarks FITBIT®, JAWBONE®, POLAR®, SAMSUNG®, APPLE® and UNDER ARMOUR®.

In the illustrated embodiment of FIG. 2, the activity tracking device 20 includes electronic circuitry comprising, one or more sensors 26, a processor 27, a memory 28, and a transmitter/receiver 29. Additionally, the activity tracking device 20 includes a protective outer shell or housing 22b designed to retain and protect various sensors and other electronic components positioned within the housing 22b. The housing 22b comprise any number of shapes, configurations, and/or materials, the description herein being merely exemplary. The activity tracking device 20 also includes a battery or other power source (not shown) configured to power the various electronic devices within the activity tracking device 20. In one embodiment, the battery of the activity tracking device 20 is a long life non-rechargeable battery designed to last longer than the expected life of the shoe 12. In one embodiment, the battery of the activity tracking device 20 is a rechargeable battery. In this embodiment, the activity tracking device 20 may be placed in or connected to a battery charger configured for use with the activity tracking device 20 in order to recharge the battery.

With continued reference to FIGS. 1-2, the activity tracking device 20 may also include other features visible on the housing 22b, such as buttons 23, a display screen 24, one or more connection ports (not shown), or other input/output hardware and software that operate in conjunction with an I/O interface 25. In the embodiment shown, the buttons 23 comprise tactile buttons, switches, and/or toggles. However, in other embodiments, the buttons 23 may also comprise capacitive or resistive touch sensor. The display screen 24 may vary based on the type of device. For example, in the embodiment shown, the display screen 24 comprises an LCD or LED screen that provides performance metric information (e.g., time, distance, pace, heart rate, progress toward a goal, or some combination thereof, etc.), notifications, text messages, caller ID, etc. to the user. In some embodiments, the display screen 24 is a touch screen display that allows the user to provide inputs to the I/O interface 25 via virtual buttons or other interfaces on the touch screen. Alternatively, in one embodiment, the display screen 24 may simply be one or more colored lights and/or flashing patterns configured to communicate information to the user (e.g., progress towards a goal or other performance metric). The connection ports may be used to connect the activity tracking device 20 to a power source or to share data with other electronic devices.

The fitness data accumulated during an activity or workout may be collected automatically by the sensors 26 of the activity tracking device 20, via manual entry by the user, and/or collected by any of various other means. The sensors 26 of the activity tracking device 20 may comprise any of various devices configured to collect the fitness data, including step data, other motion data, distance traversal data, pace data, GPS data, altitude data, heart rate data, breathing data, environmental/positional data, and/or any of various other types of fitness data that may be relevant to determining activities of the wearer. In at least one embodiment, the sensors 26 of the activity tracking device 20 includes a 3-axis accelerometer configured to detect the motions of the wearer during running or walking, in particular the user's gait or form while running or walking. Of course, it will be recognized by those of ordinary skill in the art that numerous other sensors may be used, depending on the type of activity the activity tracking device 20 is designed to detect.

The processor 27 may be any of various microprocessors as will be recognized by those of ordinary skill in the art. The processor 27 is connected to the sensors 26, the I/O interface 25, the memory 28, and the transmitter/receiver 29, and is configured to deliver data to and/or receive data from each of these components. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 28 is configured to store data and program instructions that, when executed by the processor, enable the activity tracking device 20 to perform various operations described herein. The data generally includes fitness data, but may also include various types of operational data that may be ancillary to the basic operation of the activity tracking device 20. The instructions stored at the memory 28 generally include firmware and/or software for execution by the processor 27. Such instructions may be present on the device 20 at the time of manufacture or may be downloaded thereto via well-known mechanisms. In one embodiment, the instructions stored in the memory 28 include a client-side activity tracking application, discussed in greater detail below, which acts as companion software to the client-side activity tracking application of the personal electronic device 30 and is executed by the processor 27 to process fitness data and present the fitness data in a graphical format on the display screen 24. The memory 28 may be of any type capable of storing information accessible by the processor 27, such as a memory card, ROM, RAM, write-capable, read-only memories, or other computer-readable medium.

The transmitter/receiver 29 in one embodiment comprises an RF transmitter and receiver configured to transmit and receive communications signals over a short range using a wireless communications technology, such as Wi-Fi or Bluetooth®, using any of various communications protocols, such as TCP/IP. Such transmitter/receivers are well known and will be recognized by those of ordinary skill in the art. The transmitter/receiver 29 is particularly configured to communicate with the personal electronic device 30 when respective activity tracking device 20 is within a given range of the personal electronic device 30, and transmit collected fitness data to the personal electronic device 30.

System Server

With continued reference to FIGS. 1-2, the remote system server 40. The system server 40 is typically provided in a housing, cabinet or the like 42 that is configured in a typical manner for a server or related computing device. In the illustrated embodiment of FIG. 2, the system server 40 includes a processor 47, memory 48, and a network communications module 49. However, it should be appreciated that the embodiment of the system server 40 shown and described is only one exemplary embodiment of a system server 40. As such, the exemplary embodiment of the system server 40 is merely representative of any of various manners or configurations of system servers or other data processing systems that are operative in the manner set forth herein.

The processor 47 of the system server 40 may be any of various processors as will be recognized by those of ordinary skill in the art. The processor 47 is operably connected to the memory 48 and the network communications module 49, and is configured to deliver data to and/or receive data from each of these components. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 48 is configured to store data and program instructions that, when executed by the processor 47, enable the system server 40 to perform various operations described herein. The data may include, for example, fitness data 44, which is related to the activities, workouts, health and fitness profiles, etc. of a plurality of users, along with other operational data that may be ancillary to the basic operation of the system server 40 and any applications retained on the system server 40. The instructions stored at the memory 48 generally include firmware, an operating system, and/or other software for execution by the processor 47. In at least one embodiment, the memory 48 is configured to store instructions including a network-side activity tracking application for execution by the processor 47, as well as a database of fitness data use by at least the network-side activity tracking application. The memory 48 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art.

The network communications module 49 of the system server 40 provides an interface that allows for communication with any of various devices using various means. In particular, the network communications module 49 includes a local area network port that allows for communication with any of various local computers housed in the same or nearby facility. In some embodiments, the network communications module 49 further includes a wide area network port that allows for communications with remote computers over the network 50 (e.g., the Internet). Alternatively, the system server 40 communicates with the network 50 via a modem and/or router of the local area network. In one embodiment, the network communications module is equipped with a Wi-Fi transceiver or other wireless communications device. Accordingly, it will be appreciated that communications with the system server 40 may occur via wired communications or via the wireless communications. Communications may be accomplished using any of various known communications protocols.

The system server 40 may further include a power module (not shown) which is operative, adapted and/or configured to supply appropriate electricity to the system server 40 (i.e., including the various components of the system server 40). The power module may operate on standard 120 volt AC electricity, but may alternatively operate on other AC voltages or include DC power supplied by a battery or batteries.

The system server 40 may be accessed locally by an authorized user (i.e., an administrator or operator). To facilitate local access, the system server 40 may include an interactive user interface (not shown). Via the user interface, an operator may access the instructions, including the network-side activity tracking application, and may collect data from and store data to the memory 48. In at least one embodiment, the user interface may suitably include an LCD touch screen or the like, a mouse or other pointing device, a keyboard or other keypad, speakers, and a microphone, as will be recognized by those of ordinary skill in the art. Accordingly, the user interface is configured to provide an administrator or other authorized user with access to the memory 48 and allow the authorized user to amend, manipulate and display information contained within the memory.

Activity Tracking Application

The client-side activity tracking applications, stored in the memory 38 of the personal electronic device 30 and/or the memory 28 of the activity tracking device 20, at least include instructions for enabling a user to track a plurality of performance metrics during an activity or workout. Particularly, the activity tracking application includes instructions for collecting and processing fitness data during an activity or workout to provide various performance metrics to the user. The term "performance metric" as used herein refers to any standard of measurement relevant to an assessment of the performance, fitness, and health of the user during an activity or workout, or series of activities or workouts. In some cases, the raw fitness data, either measured or manually entered, is processed substantially to provide a performance metric, but in other cases, fitness data may simply be organized into a more presentable form to provide the performance metric. Performance metrics can be generally be considered a further type of fitness data, as defined above.

Some examples of performance metrics include: repetition data expressed as a number of repetitions for a particular set, exercise, or workout; weight/resistance expressed as weight/resistance for an individual repetition or set; weight/resistance and repetition data expressed as a total volume for a particular set, exercise, or workout; heart rate sensor data expressed as beats per minute during an exercise or workout; acceleration data expressed a total number of steps during an exercise or workout; GPS data expressed as a total distance traversed during an exercise or workout; GPS data expressed as positions over time and/or a route/path of the user during an exercise or workout; GPS data expressed as an speed/pace over time or average speed/pace during an exercise or workout; GPS data or altimeter data expressed as an elevation over time during an exercise or workout; fitness data expressed as an estimated number of calories burned; time data expressed a total amount of time spent during an activity or workout; and fitness data express as a total number of workouts or number of workouts during a particular time period (e.g., workouts per week). Further exemplary performance metrics may include any parameter of fitness data expressed as an average over a particular duration of time (e.g. the duration of the workout), as a data plot over the particular duration of time, as a maximum or minimum over the particular duration of time, as a value for some point in time of particular interest, or as a percentage of a user's health or fitness goal or other standard.

Data Structure for Recording Complex Workout Session Templates and Sessions

The client-side and server-side activity tracking applications advantageously utilize a versatile data structure for robustly representing complex workout session templates and recording fitness data associated with individual workout sessions. Particularly, the versatile data structure enables robust representation of many popular fitness activities, such as strength training, circuit training, and interval training, and notably arbitrary combinations thereof, which are poorly suited for conventional fitness tracking systems that are designed primarily for fitness activities that are performed continuously for a period of time.

As used herein, the phrase "workout session template" refers to a set of exercises that are organized in a particular manner that can be used as a template for a workout session. As used herein, the phrase "workout session" refers to a particular performance of a set of exercises that are organized in a particular manner. As used herein, with respect to a workout session template, the term "organization" or "organized" refers to any ordering, a grouping, hierarchy, or the like of the set of exercises that form a workout session template or a workout session.

FIG. 3 shows an exemplary set of work session templates for a fictitious user named "Jack." In FIG. 3, Jack's workout session template is illustrated in a manner in which he might record it in a notebook or on a whiteboard, and thus is illustrative of how a typical user might think about how his workout session template is structured.

As can be seen, Jack does strength training on Mondays, Wednesdays, and Fridays and, as an experience weight lifter, has three distinct workout session templates 110, 120, and 130 which he has named "Push Day," "Pull Day," and "Leg Day." In each case, Jack warms up with 5 minutes of stretching and 5 minutes of foam rolling, performs three different types of strength training exercises as his workout, and then cools down by walking for 5 minutes. However, the particular strength training exercises performed varies for each of his three workout session templates. Particularly, in the "Push Day" workout session template 110, Jack does the exercises: "Bench Press," "Tricep Dips," and "Shoulder Press." Additionally, in the "Pull Day" workout session template 120, Jack does the exercises: "Bicep Curls," "Lat Pulldowns," and "Bent-Over Rows." Finally, in the "Leg Day" workout session template 130, Jack does the exercises: "Squats," "Deadlifts," and "Leg Curls." For each exercise, Jack performs three sets with a defined number of repetitions. However, in the "Pull Day" workout session template 120, Jack performs the three exercises as circuits in which he does one set of each exercise, and then repeats until the circuit has been completed three times. In contrast, in the "Leg Day" workout session template 130, Jack sequentially performs all three sets of a particular exercise before moving on to the next exercise. In further contrast, in the "Push Day" workout session template 110, Jack performs sets for two exercises as circuits, and then performs sets for one exercise sequentially. Although, the structure of his workout remains generally consistent from week to week, the number of repetitions and the weight changes on a regular basis as Jack's performance increases over time. Additionally, individual workout sessions can diverge from the intended workout session template when faced with unexpected constraints, such as equipment availability.

Additionally, Jack does cardio on Tuesdays and Thursday. However, as a novice runner, he does a "Running Intervals" workout session template 140 rather than run continuously for his entire workout. Particularly, Jack warms up with 5 minutes of walking. For his workout, Jack runs 5 minutes, then walks 3 minutes, then runs 8 minutes, then walks 3 minutes, and then runs 5 minutes. Finally, Jack cools down with 5 minutes of walking. Jack utilizes the same pattern of intervals each day until he becomes comfortable with the pattern, and then he moves on to a more challenging pattern of intervals according to a progression that incrementally builds towards a continuous run for the workout. Thus, the "Running Intervals" workout session template 140 periodically changes to include intervals of different durations, as well as different numbers of intervals.

It should be appreciated that these workout session templates are not easily or robustly represented using conventional fitness tracking systems. Particularly, using many conventional fitness tracking systems Jack can only record his workout sessions as a single continuous workout of a generic type, such as "weight lifting" or "running." Although this might be easy to do, it does not provide a robust and detailed representation of his workout sessions. Alternatively, using a many conventional fitness tracking systems Jack can record his workout sessions as a chronological sequence of unrelated individual sessions corresponding to each set of repetitions in his strength training workout session templates, or corresponding to each interval in his cardio workout session templates. Although, this would provide a somewhat more detailed record of his workout, it is quite cumbersome to do and still lacks some important details. Particularly, in either case, conventional fitness tracking systems do not easily enable Jack to record what his intended goals were for each exercise, what his actual performance was, and how each exercise fits together with the others to form a coherent workout session template.

The versatile data structure described herein solves these problems with conventional fitness tracking systems by enabling complex workout session templates to be represented robustly and enabling detailed fitness data associated with particular workout sessions to be recorded in association with complex workout session templates in a manner that enables detailed analysis and a less cumbersome user experience.

Figure 4A:
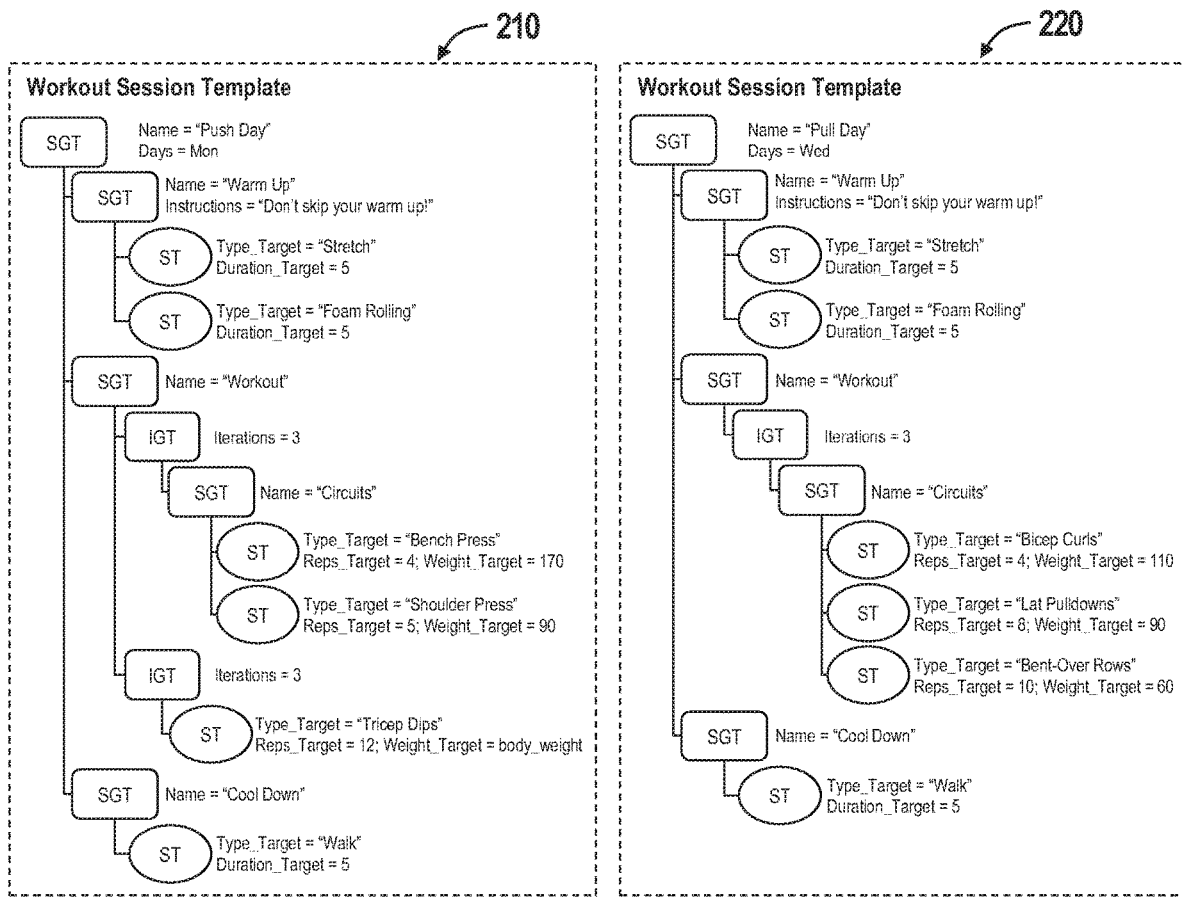
FIG. 4A-B show data structures for storing workout session templates, which represent the exemplary workout session templates illustrated in FIG. 3.
Figure 4B:
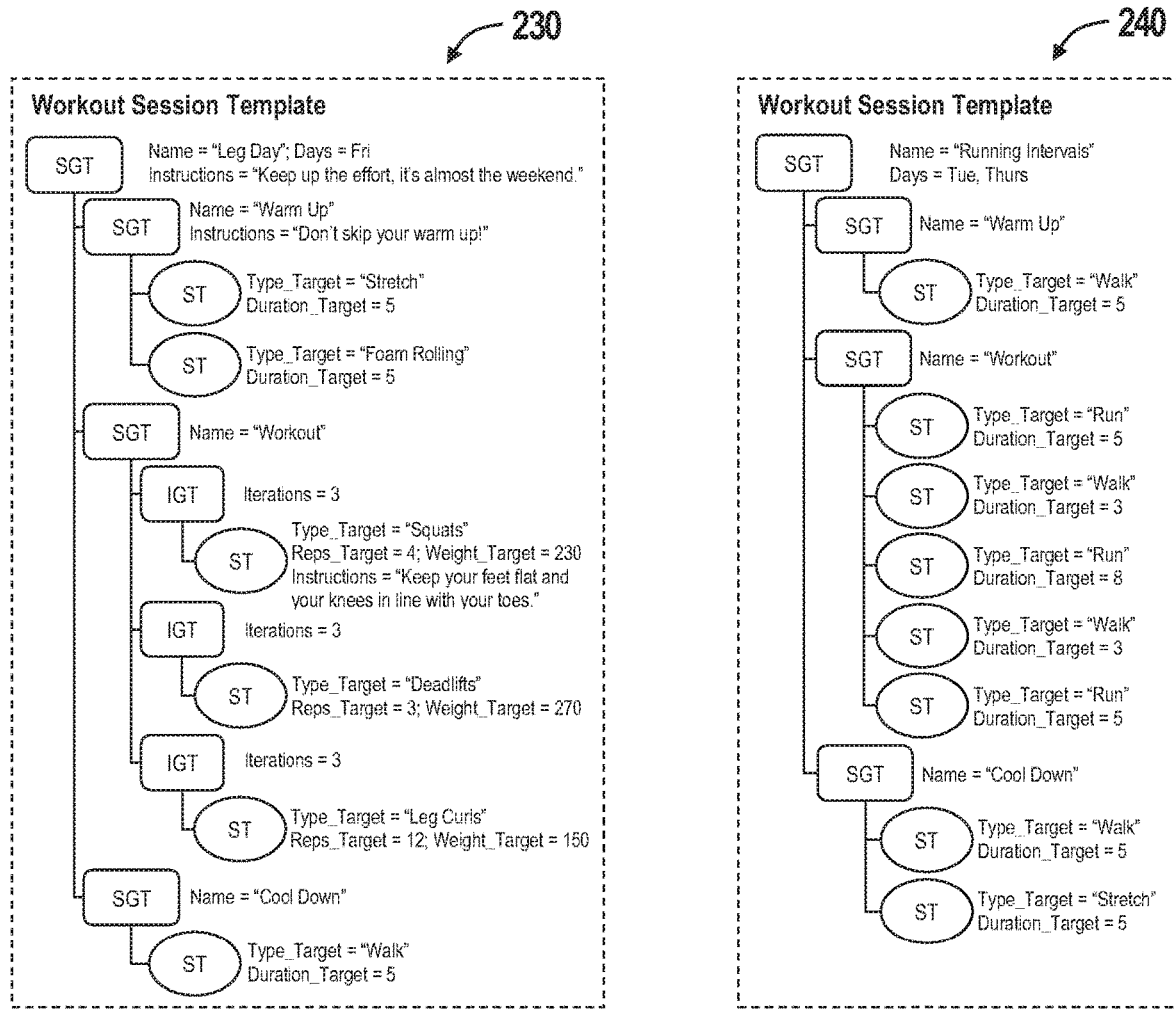

FIGS. 4A and 4B show workout session template data structures 210, 220, 230, and 240 for storing fitness data, which represent to the exemplary workout session templates illustrated in FIG. 3. As discussed in greater detail below, essentially similar data structures can also be used for storing fitness data associated with particular workout sessions. In each case, the workout session template data structures 210, 220, 230, and 240 have a tree-like data structure (referred to herein simply as a "tree structure") comprised of a plurality of nodes with parent and child relationships defined between the nodes. The workout session template data structures 210, 220, 230, and 240 have at least two types of nodes: "segment template" nodes and "group template" nodes. As used herein, a "segment template" node refers to a node of a tree structure that represents a period of performance of a particular type of exercise to be performed and is illustrated as an oval with the label "ST" for "segment template." In at least one embodiment, a segment template node represents a period of continuous performance of a particular type of exercise to be performed. For example, the workout session template data structure 210 includes six segment template nodes, representing the six different exercises that are performed in the "Push Day" workout session template 110 (i.e., "Stretch," "Foam Rolling," "Bench Press," "Shoulder Press," "Tricep Dips," and "Walk."). The segment template nodes never have any child nodes and, thus, represent the most atomic element in the data structure. In contrast, as used herein, a "group template" node refers to a node of a tree structure that represents a logical and/or hierarchical grouping of one or more segment template nodes (representing one or more exercises) and/or group template nodes (representing one or more groups of exercises) and is illustrated as a rounded rectangle. More particularly, each group template node has at least one child, which may be an arbitrary combination of one or more segment template nodes and/or one or more group template nodes. In general, the group template nodes represent the manner in which the user thinks about his or her work being logically or hierarchically organized.

In the illustrated embodiment, workout session template data structures 210, 220, 230, and 240 have two different types of group template nodes: "segment group template" nodes and "iteration group template" nodes. As used herein, a "segment group template" node refers to a node of a tree structure that represents a grouping of one or more segment template nodes (representing one or more exercises) and/or group template nodes (representing one or more groups of exercises) in a workout session template and is illustrated as a rounded rectangle with the label "SGT" for "segment group template." For example, each of workout session template data structures 210, 220, 230, and 240 have segment group template nodes that define a "Warm up" portion of the respective workout session template, a "Workout" portion of the respective workout session template, and a "Cool Down" portion of the respective workout session template. Each segment group template node has at least one child, which may be an arbitrary combination of one or more segment template nodes and/or one or more group template nodes. For example, in the workout session template data structure 210, the segment group template nodes corresponding to the "Warm up" portion and the "Cool Down" portion have segment template nodes as children. In contrast, the segment group template node corresponding to the "Workout" portion has further group template nodes as children.

As used herein, an "iteration group template" node, which can be considered a special type of segment group template node, refers to a node of a tree structure that represents a grouping of exactly one segment template node (representing exactly one exercise) or exactly one group template node (representing exactly one group of exercises) that is to be repeated for a number of iterations and is illustrated as a rounded rectangle with the label "IGT" for "iteration group template." In other words, an iteration group template node has exactly one child, which may be a segment template node or a group template node. For example, in the workout session template data structure 210, the segment group template node corresponding to the "Workout" portion has two iteration group template nodes as children. A first of the two iteration group template nodes in the workout session template data structure 210 has a segment group template node corresponding to a "Circuits" portion of the workout session template in which the "Bench Press" and "Shoulder Press" segments/exercises are repeated as a circuit for three iterations. A second of the two iteration group template nodes in the workout session template data structure 210 has only the "Tricep Dips" segment/exercise as a child, which is repeated sequentially for three iterations.

As can be seen the workout session template data structures 210, 220, 230, and 240 provide a much more robust representation of a workout session template by incorporated logical and hierarchical groups that reflect the manner in which the user thinks about his or her work being organized, because the groups are user-defined. This is in contrast to conventional fitness tracking systems in which the workout session templates are, at best, represented as a list of unrelated individual exercises or a single monolithic activity representing the entirety of the workout session template.

In addition to providing a much more robust representation of a workout session template, the workout session template data structures 210, 220, 230, and 240 provide a framework for storing information about the workout session template and for storing fitness data associated with particular workout sessions in which the user performed the workout session template. Particularly, the workout session template data structures 210, 220, 230, and 240 store values and/or data for one or more attributes associated with each node in the respective data structure. In the illustrations of FIGS. 4A and 4B, exemplary attributes are shown to the right of the node to which the attributes belong. The group template nodes may have a variety of different attributes that provide define or otherwise provide information regarding the particular portion of the workout session template. For example, in the illustrated workout session template data structures 210, 220, 230, and 240, the top level segment group template nodes have a "Name" attribute that stores a user defined name (e.g., "Push Day") for the workout session template and a "Days" attribute that stores the days in which the user intends to or typically performs the workout session template. Similarly, the additional segment group template nodes also have a "Name" attribute that stores a user defined name (e.g., "Warm Up," "Workout," and "Cool Down") for the particular section within the workout session template. The iteration group template nodes may have an "Iterations" attribute that stores the number of iterations that are performed for the exercises defined by the child segment template nodes. Alternatively, or in addition, the iteration group template nodes may have "Duration" attribute that stores an amount of time that the exercises defined by the child segment template nodes are iteratively performed. In this way, the iteration group template nodes may flexibly define the duration but leave the number of iterations undefined, may define the number of iterations but leave the duration undefined, or define both the number of iterations and the duration. It should be appreciated, however, that these attributes described herein and illustrated in the figures are merely exemplary and that group template nodes may have any other attributes that might be useful in the fitness tracking system 10.

Likewise, the segment template nodes also include a variety of different attributes that define or otherwise provide information regarding the particular exercise to be performed during the respective segment of the workout session template. For example, in the illustrated workout session template data structures 210, 220, 230, and 240, each segment at least has a "Type_Target" attribute that stores the type of exercise (e.g., "Stretch," "Bicep Curls," "Squats," etc.) that is to be performed during the segment. Additionally, each segment template node includes a variety of attributes that define performance goals, which generally differ depending on the type of exercise performed during the segment. For example, in the illustrated workout session template data structures 210, 220, 230, and 240, the segment template nodes corresponding to warm up and cardio exercise types (e.g., "Stretch," "Foam Rolling," "Walk," and "Run") each have a "Duration_Target" attribute that stores a target and/or goal amount of time that the respective exercise is performed during that particular segment of the workout session template. In contrast, the segment template nodes corresponding to strength training exercise types (e.g., "Shoulder Press," "Lat Pulldowns," "Deadlifts," etc.) each have a "Reps_Target" attribute that stores a target and/or goal number of repetitions in each set performed of the exercise. Additionally, the segment template nodes corresponding to strength training exercise types have a "Weight_Target" attribute that stores a target and/or goal amount of weight and/or resistance used for each repetition. It should be appreciated, however, that these attributes described herein and illustrated in the figures are merely exemplary and that segment template nodes may have any other attributes that might be used for a particular type of exercise. Other attributes that might belong to a segment template node include attributes related to pace, time, distance, heart rate ranges, steps, and rest times (between repetitions, sets, etc.). Additionally, a user may arbitrarily associate attributes of any type with a segment template node. For example, strength training exercise types may include the "Reps_Target" and "Weight_Target" attributes by default, but a user could choose to utilize any other attributes that they would like, such as utilizing a "Distance_Target" attribute for a "Bench Press" exercise.

In some embodiments, attributes may be arbitrarily applied to any of the nodes in the workout session template data structures 210, 220, 230, and 240, and have a different meaning depending on the particular node with which they are associated. For example, some nodes in the workout session template data structures 210, 220, 230, and 240 include an "Instructions" attribute that includes, for example, user-generated free-form text instructions or notes. In the illustrated examples, the segment group template nodes corresponding to the "Warm Up" sections of the strength training workout session templates stores an "Instructions" attribute having the value "Don't skip your warm up!" which reminds the user of the importance of warming up before weight lifting. Similarly, the top level segment group template node for the "Leg Day" workout session template stores an "Instructions" attribute having the value "Keep up the effort, it's almost the weekend." which motives the user on his Friday workout sessions. Finally, the segment template node for the "Squats" exercise stores an "Instructions" attribute having the value "Keep your feet flat and your knees in line with your toes." which reminds the user to maintain proper form for his squats exercise. As can be seen, the "Instructions" attribute can be applied to segments or groups and has different meaning depending on where it is stored.

In some embodiments, some attributes, in particular those relating to a target and/or goal performance, may store variable or relative values such as "Heavy," "Light," "Fast," "Slow," or percentage values. At the time of a particular workout session, suggested values can be populated according to the variable or relative values based stored fitness data relating to past performance or the like. For example, the relative value "Heavy" as applied to a "Weight_Target" attribute might be automatically populated with a value equal to 80% of the user's current one-rep maximum weight for the particular exercise. Additionally, for certain types of exercises (e.g., body weight exercises, such as "Tricep Dips"), a variable may be populated as a function of current user profile information (e.g., the variable body_weight, for the "Tricep Dips").

Additional exemplary attributes that might be defined in relation to the various group template nodes or segment template nodes are attributes relating to how the exercises are performed. For example, an iteration group template node and/or segment group template node might have a "Super Set" attribute that indicates that each exercise(s) is performed without rest between exercise sets in a circuit. Similarly, an iteration group template node might have a "Drop Set" attribute that indicates that the iterations of the exercise(s) are performed with successively lighter weights or otherwise lower resistance. Additionally, an iteration group template node, segment group template node, or segment might have an "EMOM" attribute that indicates that each set of repetitions is performed every minute, on the minute, with short rest periods therebetween. Finally, an iteration group template node, segment group template node, or segment might have "AMRAP" attribute that indicates that, for each set, the user should perform as many repetitions as possible before failure.

Figure 4C:
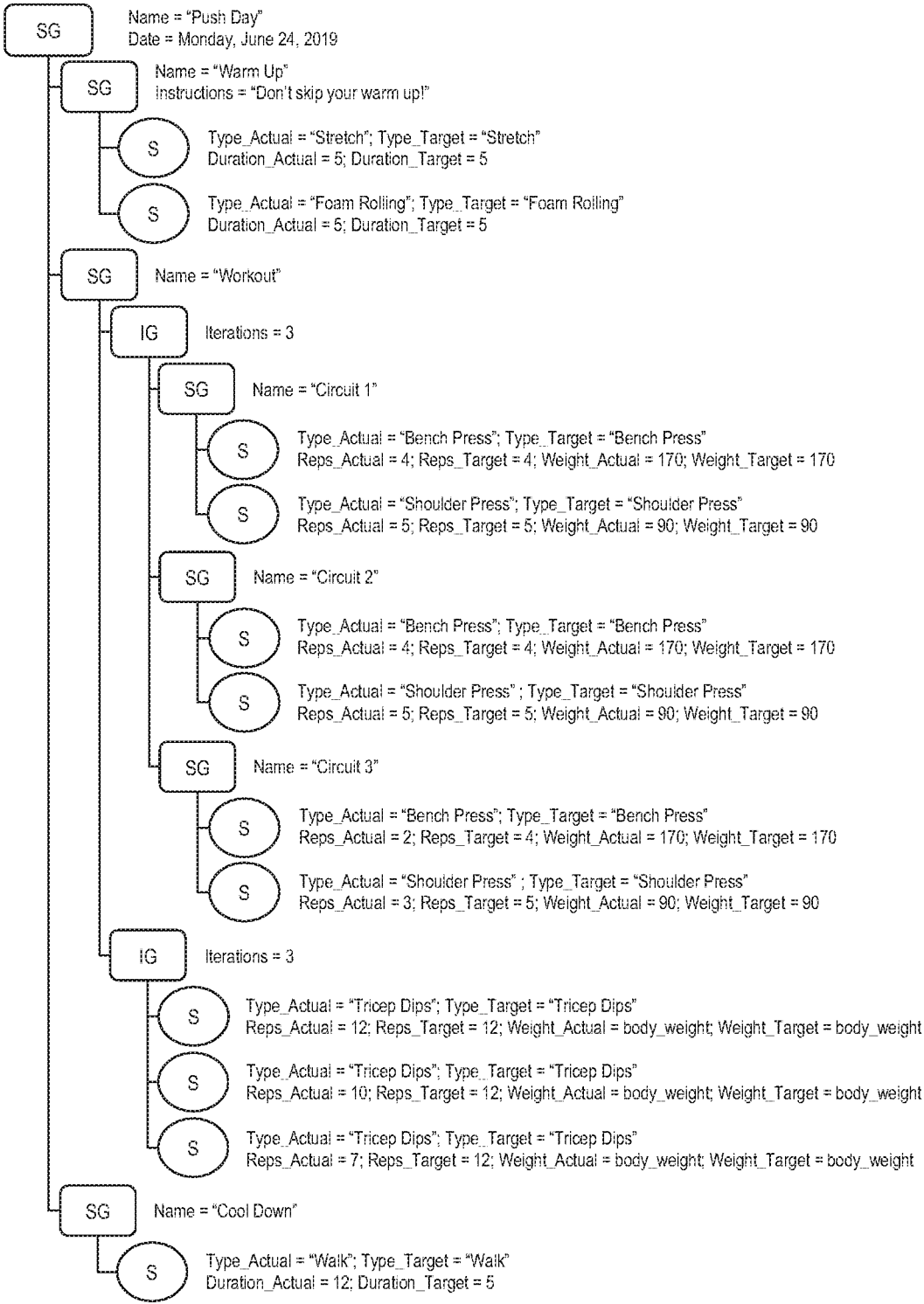
FIG. 4C shows a data structure for storing fitness data, which represents an exemplary workout session in which the user performed one the workout session templates illustrated in FIG. 3.

As noted above, the versatile data structures described herein are not only useful for representing a workout session template, but can also be used to store fitness data corresponding to individual workout session in which the user performed a workout based on the workout session template. FIG. 4C shows a workout session data structure 250 that represents an exemplary workout session performed by a user, using the "Push Day" workout session template. The workout session data structure 250 is similar to the workout session template data structure 210 of FIG. 4A representing the "Push Day" workout session template and is derived therefrom. Accordingly, the features shared between the workout session data structure 250 and the workout session template data structure 210 are not described again in complete detail.

In order to generate the workout session data structure 250 based on the workout session template data structure 210, each node of the workout session template data structure is converted to its workout session counterpart. Particularly, each segment template node is converted to a "segment" node, each group template nodes is converted to a "group" node, each segment group template node is converted to a "segment group" node, and each iteration group template node is converted to an "iteration group" node. As used herein, a "segment" node refers to a node of a tree structure that represents a period of performance of a particular type of exercise during a workout session and is illustrated as an oval with the label "S" for "segment." In at least one embodiment, a segment template node represents a period of continuous performance of a particular type of exercise during a workout session. As used herein, a "group" node refers to a node of a tree structure that represents a logical and/or hierarchical grouping of one or more segment nodes (representing one or more exercises) and/or group nodes (representing one or more groups of exercises) in a workout session and is illustrated as a rounded rectangle. More particularly, as used herein, a "segment group" node refers to a node of a tree structure that represents a grouping of one or more segment nodes (representing one or more exercises) and/or group nodes (representing one or more groups of exercises) in a workout session and is illustrated as a rounded rectangle with the label "SG" for "segment group." As used herein, an "iteration group" node, which can be considered a special type of segment group node, refers to a node of a tree structure that represents a grouping of at least one segment node (representing at least one exercise) or at least one group node (representing at least one group of exercises) that was repeated for a number of iterations during a workout session and is illustrated as a rounded rectangle with the label "IG" for "iteration group."

Importantly, compared to the workout session template data structure 210, the segment nodes or segment group nodes that belong to each iteration group node have been replicated based on the number of iterations of the iteration group node. Thus, in the workout session data structure 250, in the first iteration group node, the "Circuits" segment group having "Bench Press" and "Shoulder Press" segments has been replicated three times, corresponding to the three iterations of the first iteration group node. Likewise, in the second iteration group, the "Tricep Dips" segment node has been replicated three times, corresponding to the three iterations of the second iteration group node. This enables fitness data generated or recorded during a particular workout session to be independently associated with each individual set of each exercise.

The segment nodes of the workout session data structure 250 are configured to store the target and/or goal performance related attributes that were stored in the workout session template data structure 210 as it existed prior to the workout session (i.e., the "Type_Target," "Duration_Target," "Reps_Target," and "Weight_Target" attributes). Additionally, in contrast with their counterpart segment template nodes, the segment nodes of the workout session data structure 250 are also configured to store attributes relating to an actual performance for the particular workout session (i.e., the "Type_Actual," "Duration_Actual," "Reps_Actual," and "Weight_Actual" attributes). In this way, the workout session data structure 250 stores information relating the user's intended workout session (as indicated by the workout session template) and information relating to the user's actual workout session. For example, during the example workout session represented by the workout session data structure 250, the user achieved his or her repetition targets for the first two circuits including the "Bench Press" and "Shoulder Press" exercises, but undershot his or her repetition targets in the third and final circuit, achieving only two repetitions of the "Bench Press" exercise, rather than four, and achieving only three repetitions of the "Shoulder Press" exercise, rather than five. Similarly, the user achieved his or her repetition targets for the first set of the "Tricep Dips" exercise, but undershot his or her repetition targets in the second and third sets, achieving only ten repetitions and seven repetitions in the second and third sets of the "Tricep Dips" exercise, respectively. Finally, during the "Cool Down," the user walked for twelve minutes, rather the target of five minutes.

In some cases, the workout session data structure 250 will also represent structural and/or organizational changes compared to workout session template data structure 210. For example, the user may have changed the order in which exercises were performed, changed the types of exercises that were performed, or changed the grouping and/or organization of the exercises within the workout session. The workout session data structure 250 is adapted to reflect these changes, as well as store information regarding the original intended organization of the corresponding workout session template as it existed prior to the workout session.

In some embodiments, the segment nodes of a data structure representing a particular workout session may include additional attributes, which do not have corresponding target values stored in the data structure representing the workout session template. In some embodiments, the segment nodes may include attributes indicating start and end times for the respective exercise. The start and end times can be used to retrieve additional fitness data recorded by the activity tracking device 20 or the personal electronic device 30 while that particular exercise was performed. In some embodiments, such additional fitness data may be stored in association with the respective segment node in a corresponding attribute.

In some embodiments, the workout session template data structures and the workout session data structures discussed above may store additional metadata that is not associated with any particular node, such as a creation time for a workout session template, information indicating the user who originally created a workout session template, and time of performance for a workout session.

Methods for Generating or Acquiring Complex Workout Session Templates

Methods for operating the fitness tracking system 10 are described below. In particular, methods of operating the personal electronic device 30 and/or the activity tracking device 20 to generate or otherwise acquire a complex workout session template. In the description of the methods, statements that a method is performing some task or function refers to a controller or general purpose processor executing programmed instructions stored in non-transitory computer readable storage media operatively connected to the controller or processor to manipulate data or to operate one or more components in the fitness tracking system 10 to perform the task or function. Particularly, the processor 37 of the personal electronic device 30, the processor 47 of the system server, and/or the processor 27 of the activity tracking device 20 above may be such a controller or processor. Alternatively, the controller or processor may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Figure 5:
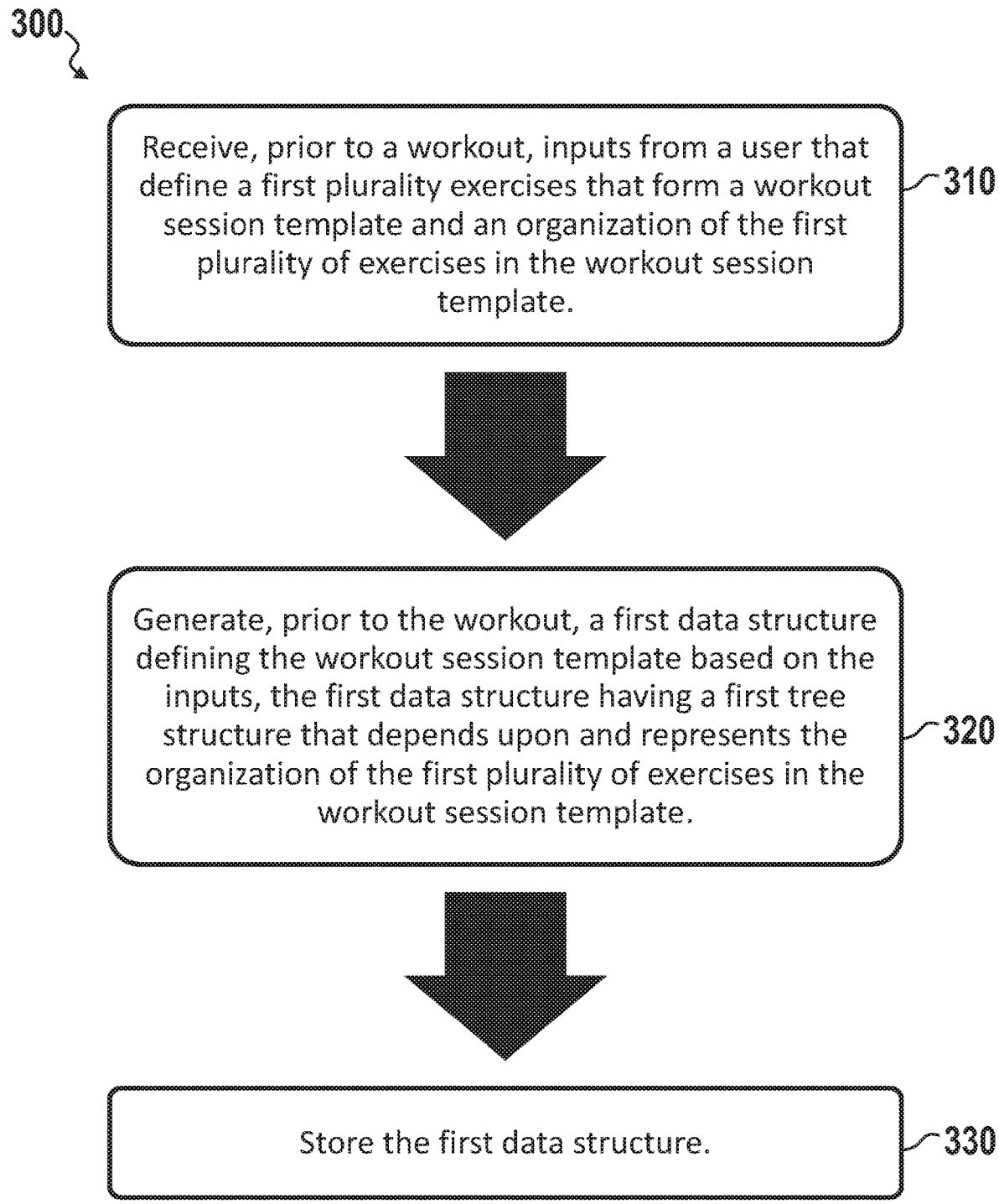
FIG. 5 shows a logical flow diagram for a method of generating a workout session template.

FIG. 5 shows a logical flow diagram for a method 300 of collecting fitness data for a user during a workout session. Particularly, the method 300 provides a method for generating a workout session template data structure having the versatile structure described above. It should be appreciated that, although the method 300 is discussed below primarily with respect to the processor 37 of the personal electronic device 30, the processor 27 of the activity tracking device 20, which may be provided in the form of a so-called "smart" watch, may also execute instructions of a client-side activity tracking application to perform some or all of the steps of the method 300. Additionally, in some embodiments, the processor 47 of the system server 40 may execute instructions of a network-side activity tracking application to perform certain steps of the method 300.

The method 300 begins with a step of receiving, prior to a workout, inputs from a user that define a first plurality exercises that form a workout session template and an organization of the first plurality of exercises in the workout session template (block 310). Particularly, with respect to the embodiments described in detail herein, the processor 37 of the personal electronic device 30 is configured to execute instructions of the client-side activity tracking application to operate the I/O interface 36 and/or the transmitter/receiver 39 to receive a plurality of inputs from a user that define a workout session template. The plurality of inputs at least includes inputs defining a particular set of exercises that form the workout session template. The plurality of inputs includes at least some information regarding an organization of the exercises in the workout session template. In at least some embodiments, plurality of inputs also include a target value for at least one performance metric with respect to at least one of the exercises that form the workout session template. However, target values need not be provided by the user.

As can be seen in the workout session templates shown in FIG. 3 and discussed in detail above, workout session templates can have a complex organization including multiple sections (e.g., "Warm Up," "Workout," and "Cool Down"), an ordering of the sections, an ordering of exercises within sections, and repetition of exercises in particular sections or groupings for a defined number of iterations. Thus, in at least some embodiments, the plurality of inputs include inputs defining the groups of exercises and inputs defining that certain groups of exercises or certain individual exercises are repeated for a particular number of iterations.

In at least one embodiment, the processor 37 of the personal electronic device 30 is configured to operate the I/O interface 36 to display a graphical user interface on the display screen 34. The user provides the plurality of inputs by interacting with the graphical user interface by, in the case of a touch screen 34, touching, tapping, swiping, or the like on the screen 34, or by operating some other user interface to interact with the graphical user interface.

Figure 6A:
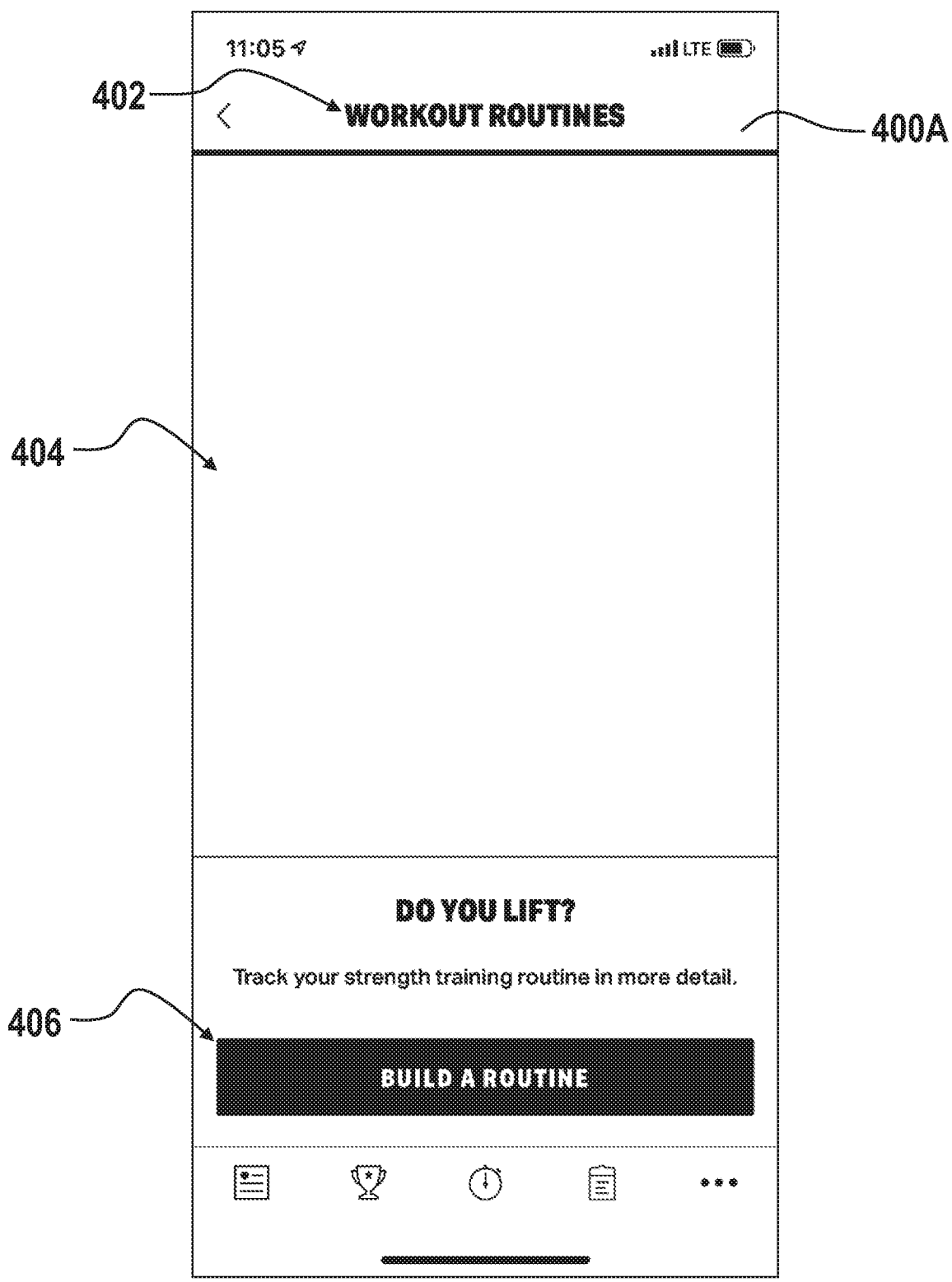
FIG. 6A-D show exemplary graphical user interfaces for designing a workout session template.

FIG. 6A shows an exemplary embodiment of a workout session template selection screen 400A displayed on the display screen 34 of the personal electronic device 30. It will be appreciated, however, that an analogous workout session template selection screen can be displayed on the activity tracking device 20. The workout session template selection screen 400A includes a title 402 (e.g., "Workout Routines"). Additionally, the workout session template selection screen 400A includes a workout session template selection region 404. As shown, the workout session template selection region 404 is empty because the user has not yet designed any workout session templates. Finally, the workout session template selection screen 400A includes a workout session template creation option 406, which can be pressed by the user to display a workout session template creation screen that enables the user to design a workout session template. Particularly, in response to the user pressing or otherwise selecting the workout session template creation option 406, the processor 37 is configured to operate the I/O interface 36 to display a workout session template creation screen on the display screen 34.

Figure 6B:
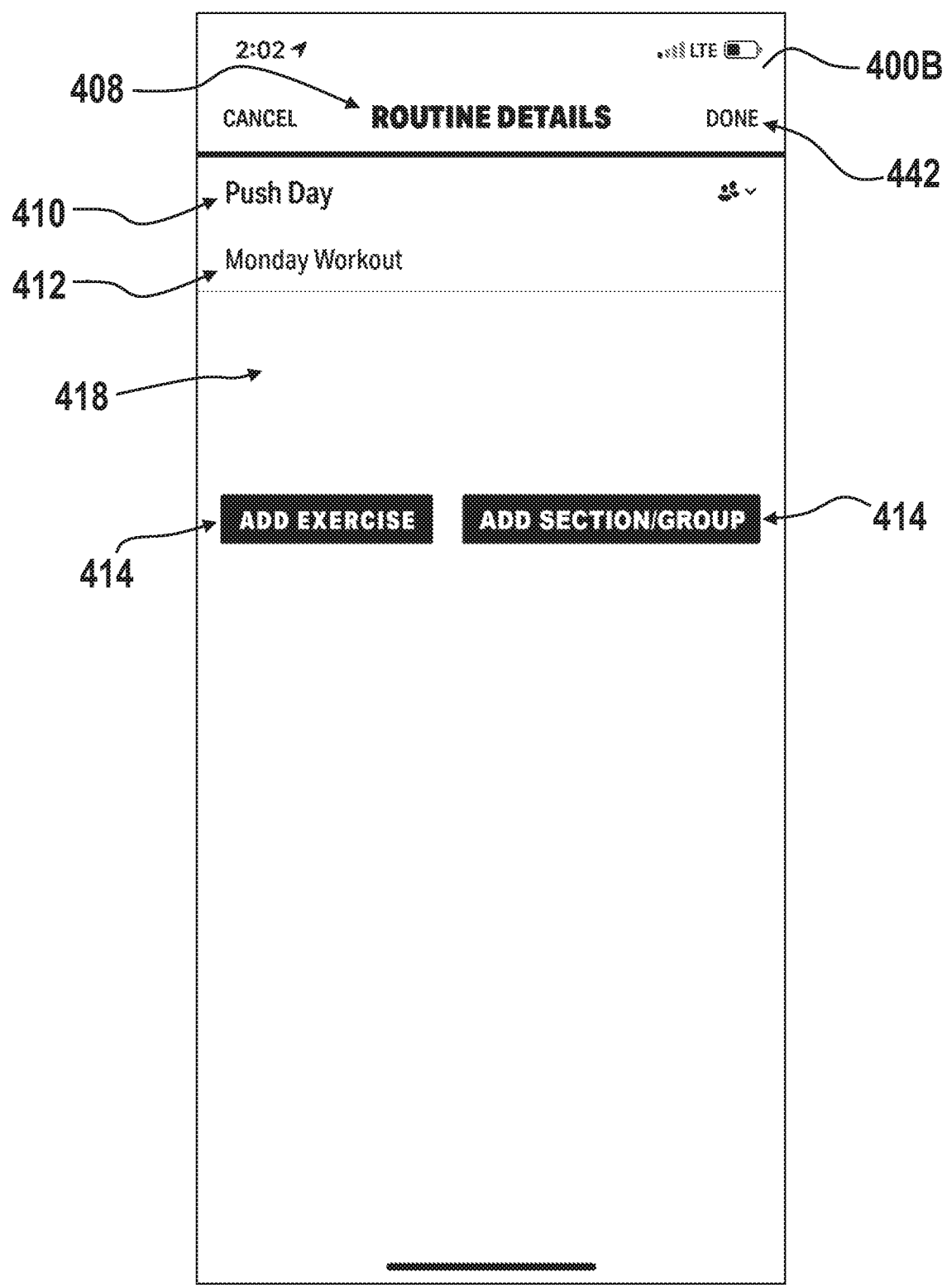

FIG. 6B shows an exemplary embodiment of a workout session template creation screen 400B displayed on the display screen 34 of the personal electronic device 30. It will be appreciated, however, that an analogous workout session template creation screen can be displayed on the activity tracking device 20. The workout session template creation screen 400B includes a title 408 (e.g., "Routine Details"). Additionally, the workout session template creation screen 400B includes a name field 410 via which the user can enter a name for the workout session template (e.g., "Push Day") and a description field 412 via which the user can enter a description for the workout session template (e.g., "Monday Workout").

The workout session template creation screen 400B includes an add exercise option 414 and an add section/group option 416, via which the user can add exercises to the workout session template and can establish groups of exercises, which will be populated in a workout session template design region 418. Particularly, in response to the user pressing or otherwise selecting the add exercise option 414, the processor 37 is configured to operate the I/O interface 36 to display one or more menus (not shown) to enable the user to search for and/or select an exercise to be added to the workout session template. Similarly, in response to the user pressing or otherwise selecting the add section/group option 416, the processor 37 is configured to operate the I/O interface 36 to display one or more menus (not shown) to enable the user to define one or more sections of the workout session template and/or groups of exercises within the workout session template.

Figure 6C:
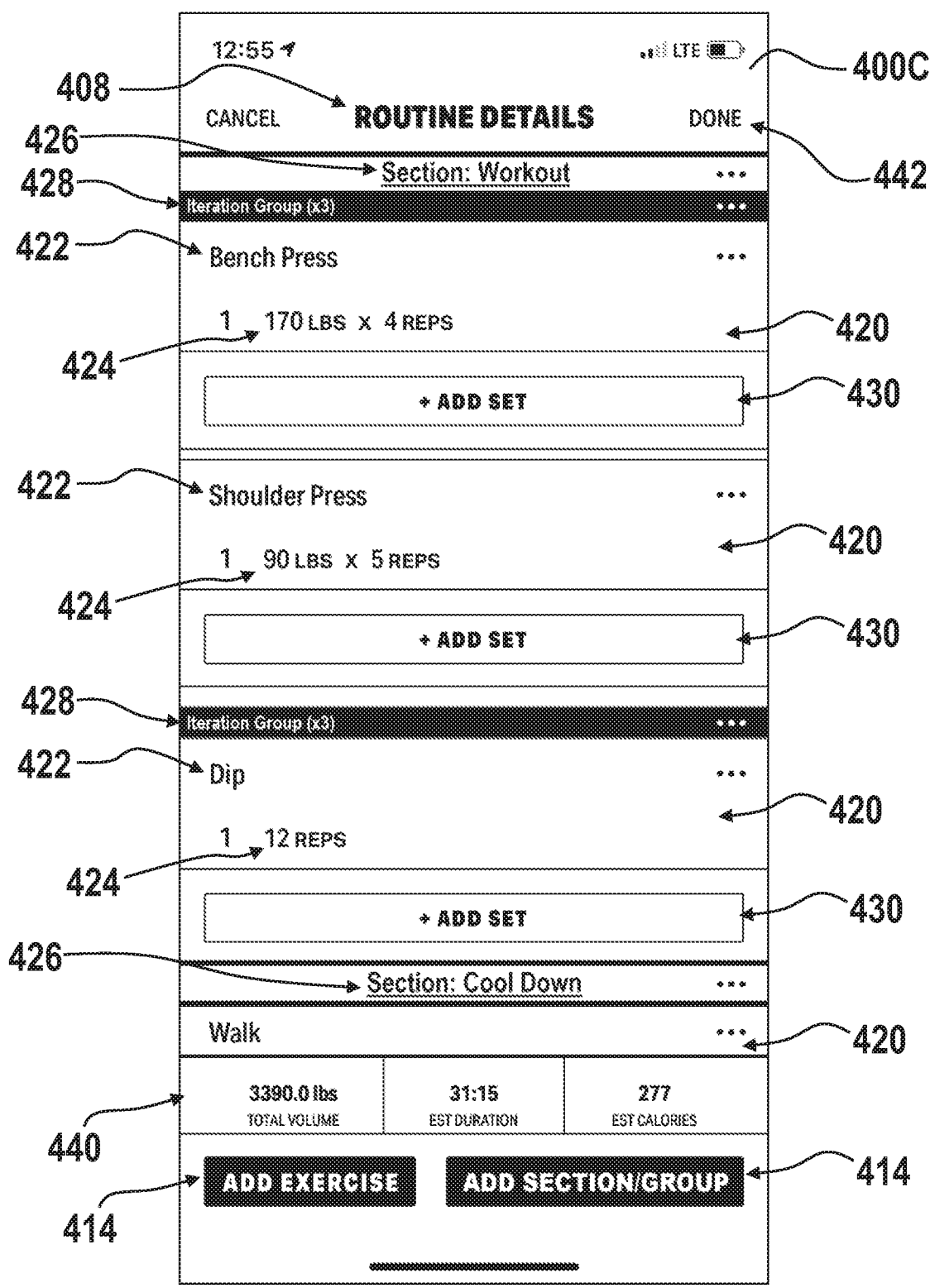

FIG. 6C shows an exemplary embodiment of a further workout session template creation screen 400C displayed on the display screen 34 of the personal electronic device 30, in which the user has finished designing a workout session template. Particularly, as the user adds exercises and groups, the processor 37 is configured to operate the I/O interface 36 to display a visual representation of the exercises and the user-defined sections and/or groups that organize the exercises. The workout session template creation screen 400C includes exercise segments 420, each having an exercise name label 422 and performance metric fields 424. Additionally, the workout session template creation screen 400C includes group labels including section labels 426 and iteration group labels 428. A user can add a new set by pressing the add set option 430 corresponding to the particular exercise. A user can edit the performance information for a set by pressing the performance metric fields 424. Particularly, in response to the user pressing or otherwise selecting the performance metric fields 424, the processor 37 is configured to operate the I/O interface 36 to display an exercise editing screen on the display screen 34.

Figure 6D:
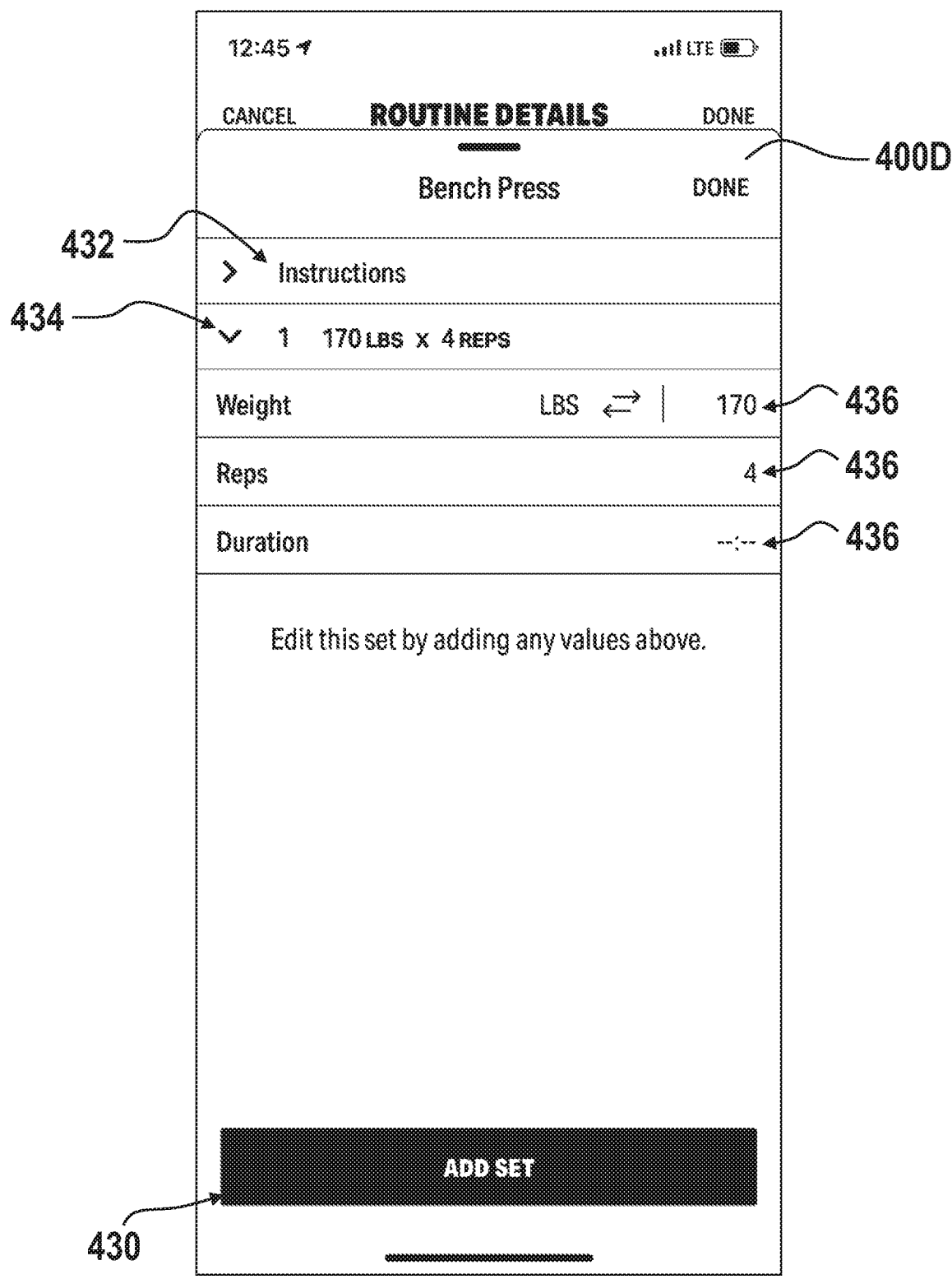

FIG. 6D shows an exemplary embodiment of an exercise editing screen 400D displayed on the display screen 34 of the personal electronic device 30. It will be appreciated, however, that an analogous exercise editing screen can be displayed on the activity tracking device 20. The exercise editing screen 400D includes an instructions field 432 via which the user can add additional information about the exercise. The exercise editing screen 400D a set section 434 having a plurality of fields 436 via which the user can enter target values for various performance metrics that are relevant the particular exercise (e.g., "Weight," "Reps," and "Duration"). It should be appreciated that the particular fields 436 and performance metrics will vary depending on the particular type of exercise for which information is being edited. When the user has finished editing information for the particular exercise, he or she can press the done option 438 to return to the workout session template creation screen.

Returning to FIG. 6C, as the user designs the workout session template and provides information about the exercise performed and target values for various performance metrics for those exercises, the processor 37 is configured to calculate estimated values for additional performance metrics for the workout session template, such as an estimated total volume, an estimated duration, and an estimated calories burned. These additional performance metrics are displayed in a workout performance section 440. Finally, when the user has finished designing the workout session template, he or she can press the done option 442 to return to the workout session template selection screen.

The method 300 continues with a step of generating, prior to the workout, a first data structure defining the workout session template based on the inputs, the first data structure having a first tree structure that depends upon and represents the organization of the first plurality of exercises in the workout session template (block 320). Particularly, with respect to the embodiments described in detail herein, the processor 37 of the personal electronic device 30 is configured to execute instructions of the client-side activity tracking application to generate a workout session template data structure that defines the workout session template based on the plurality of inputs received from the user. Particularly, the processor 37 is configured to generate the workout session template data structure in the form discussed above having a tree structure that represents the organization of the exercises in the workout session template.

As described in greater detail above, the workout session template data structure has a plurality of segment nodes corresponding to a plurality exercises that form the workout session template and a plurality of group template nodes corresponding to a plurality of groups into which the exercises are organized in the workout session template. As used herein, a "group" may include only one or multiple exercises. Each segment node is childless, whereas each group template node has at least one child including at least one segment template node or group template node. The processor 37 is configured to store any target values provided by the user for a performance metric of an exercise in the corresponding exercise node of the workout session template data structure. Additionally, in the case of iteration group template nodes, the processor 37 is configured to store the number of iterations to be performed in the corresponding iteration group template node of the workout session template data structure.

The method 300 continues with a step of storing the first data structure (block 330). Particularly, with respect to the embodiments described in detail herein, the processor 37 of the personal electronic device 30 is configured to execute instructions of the client-side activity tracking application to store the workout session template data structure that defines the workout session template in a memory. In one embodiment, the workout session template data structure is stored in a database, which may be the same as or distinct from a database that stores workout session data and other fitness data. In one embodiment, the processor 37 is configured to store the workout session template data structure locally in the memory 38. Alternatively or in addition, in some embodiments, the processor 37 is configured to operate the transmitter/receiver 39 to transmit the workout session template data structure to the system server 40. The processor 47 of the system server is configured to operate the network communications module 49 to receive the workout session template data structure and store the workout session template data structure in the memory 48.

Rather than designing workout session templates on his or her own, the user may also utilize workout session templates that are provided using other techniques. Particularly, a workout session template data structures can be retrieved from external sources or other users, or generated based on recorded fitness data or data from external sources.

Figure 7:
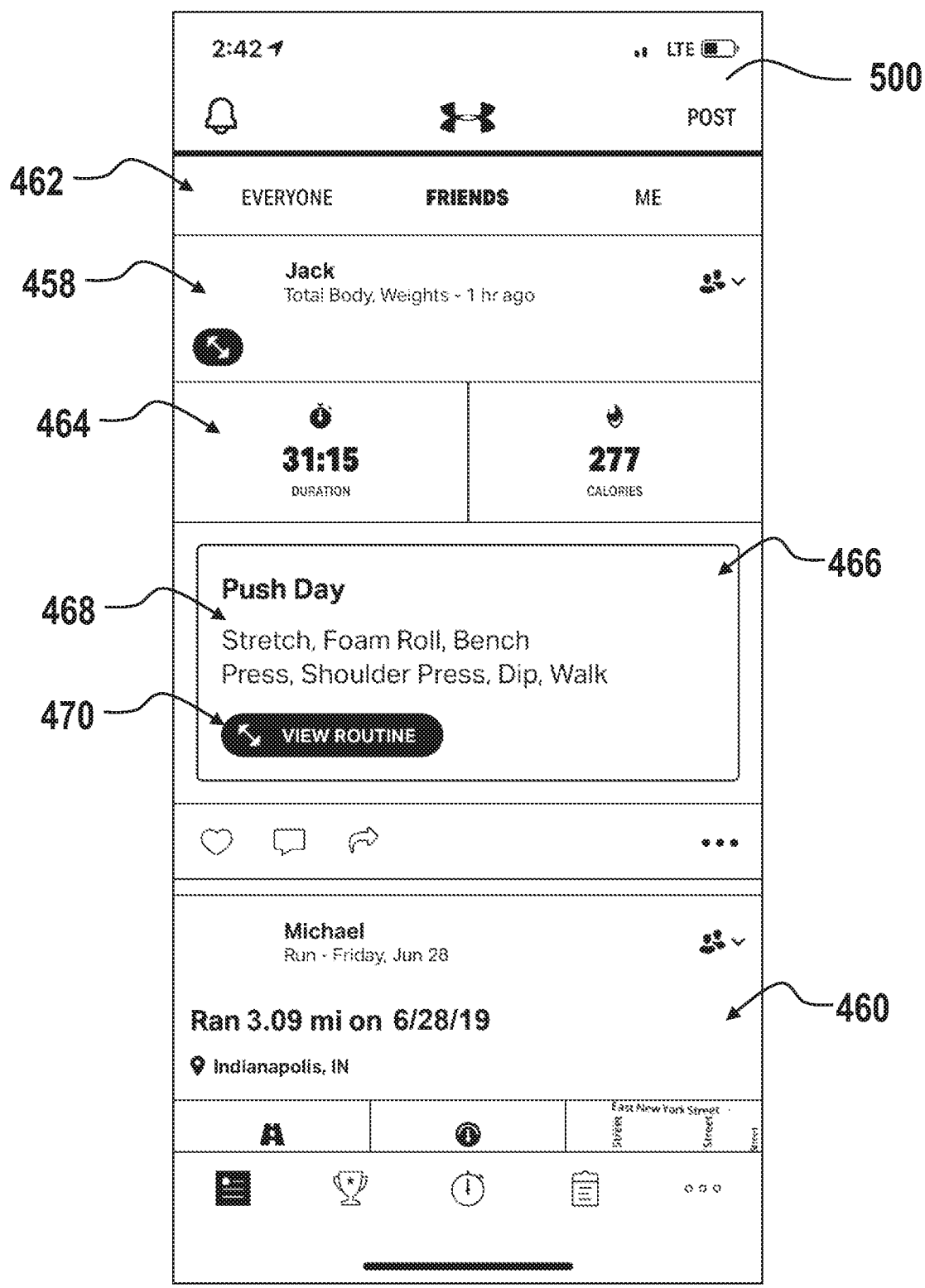
FIG. 7 shows an exemplary activity feed screen via which workout session templates can be shared.

For example, in one embodiment, users can share workout session templates with other users. Particularly, FIG. 7 shows an exemplary activity feed screen 500 displayed on the display screen 34 of the personal electronic device 30. It will be appreciated, however, that an analogous activity feed screen can be displayed on the activity tracking device 20. The activity feed screen 500 includes a list of multimedia content (which may also be referred to herein as a "feed") shared by the user, friends of the user, and other members of the community. As shown, the feed includes a workout summary 458 shared by friend of the user (e.g., "Jack"), as well as a workout summary 460 shared by the user himself (e.g., "Michael"). The activity feed screen 500 further includes filter options 462 via which the user can sort which contents are included in the feed. For example, in the embodiment shown, the user may press an "Everyone" option to show all content shared by the user, friends of the user, and other members of the community. Similarly, the user may press the "Friends" option to show only content shared by the user and friends of the user. Finally, the user may press the "Me" option to show only content shared by the user.

In the illustrated example, the workout summary 458 corresponds to a "Push Day" workout session template that was performed by Jack. The workout summary 458 includes performance metrics 464 are (e.g., a "31:15" value for the "DURATION" performance metric and a "277" value for the "CALORIES" performance metric) and a workout session template summary 466. The workout session template summary 466 includes summary information 468 and a view session template option 470 (e.g., "View Routine").

If a user would like to view a more detailed description of the workout session template or would like to download the workout session template, the user may press the view session template option 470. Particularly, in response to the user pressing or otherwise selecting the view session template option 470, the processor 37 is configured to operate the transmitter/receiver 39 to receive from the system server 40 a workout session template data structure, in the form described above, that represents the workout session template that was performed by the other user who shared their workout session (e.g., "Jack"). The processor 37 is configured to operate the I/O interface 36 to display one or more screens and/or menus (not shown) on the display screen 34 to enable to the user to view the details of the workout session template and to enable the user to save the workout session template to his or her device, e.g., such that it is available for usage on the workout session template selection screen, described above.

As another example, in some embodiments, a workout session template data structure can be generated from a body of text describing a workout session template. Particularly, in one embodiment, the processor 37 of the personal electronic device is configured to retrieve a body of text from an external source, such as from a website on the internet or from a photograph using optical character recognition techniques. The processor 37 is configured to parse or otherwise process the body of text to extract a plurality of exercises having an organization, as well any target values for performance metrics for the exercises. The processing of the body of text can be performed using any combination of natural language processing (NLP) techniques or natural language understanding (NLU) techniques known in the art, such as simple key-phrase detection and parsing or more complex neural network-based techniques, in particular recurrent neural network language processing models. Once a plurality of exercises and an organization have been extracted, the processor 37 generates a workout session template data structure in the manner described above.

As another example, in some embodiments, a workout session template data structure can be generated based on sensor data or other fitness data that was captured during a previous workout session. Particularly, the processor 37 is configured to infer plurality of exercises having an organization based on the sensor data or other fitness data that was captured during a previous workout session. As an example, based on steps data, accelerometer data, and/or heart rate data, it could be inferred that the user alternated between sprinting and walking at particular intervals. The processor 37 may be further configured to extract actual values for performance metrics, which can be used as target values for the performance metrics for the exercises in the workout session template. Once a plurality of exercises and an organization have been extracted, the processor 37 generates a workout session template data structure in the manner described above.

In the cases of extracting a workout session template based on a body of text or inferring workout session template based on sensor data or other fitness data, in some cases it may be necessary or useful to prompt the user to confirm the extracted information. For example, a body of text may utilize an ambiguous format for describing target values for certain performance metrics such that it is unclear which value corresponds to which performance metric. A user's response to a prompt can be applied to the remainder of the extracted information such that the user is not repeatedly prompted to confirm analogous ambiguities in the extracted information.

Methods for Recording Fitness Data for Complex Workout Sessions

Methods for operating the fitness tracking system 10 are described below. In particular, methods of operating the personal electronic device 30 and/or the activity tracking device 20 to collect and store fitness data during a workout session corresponding to a complex workout session template. In the description of the methods, statements that a method is performing some task or function refers to a controller or general purpose processor executing programmed instructions stored in non-transitory computer readable storage media operatively connected to the controller or processor to manipulate data or to operate one or more components in the fitness tracking system 10 to perform the task or function. Particularly, the processor 37 of the personal electronic device 30, the processor 47 of the system server, and/or the processor 27 of the activity tracking device 20 above may be such a controller or processor. Alternatively, the controller or processor may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Figure 8:
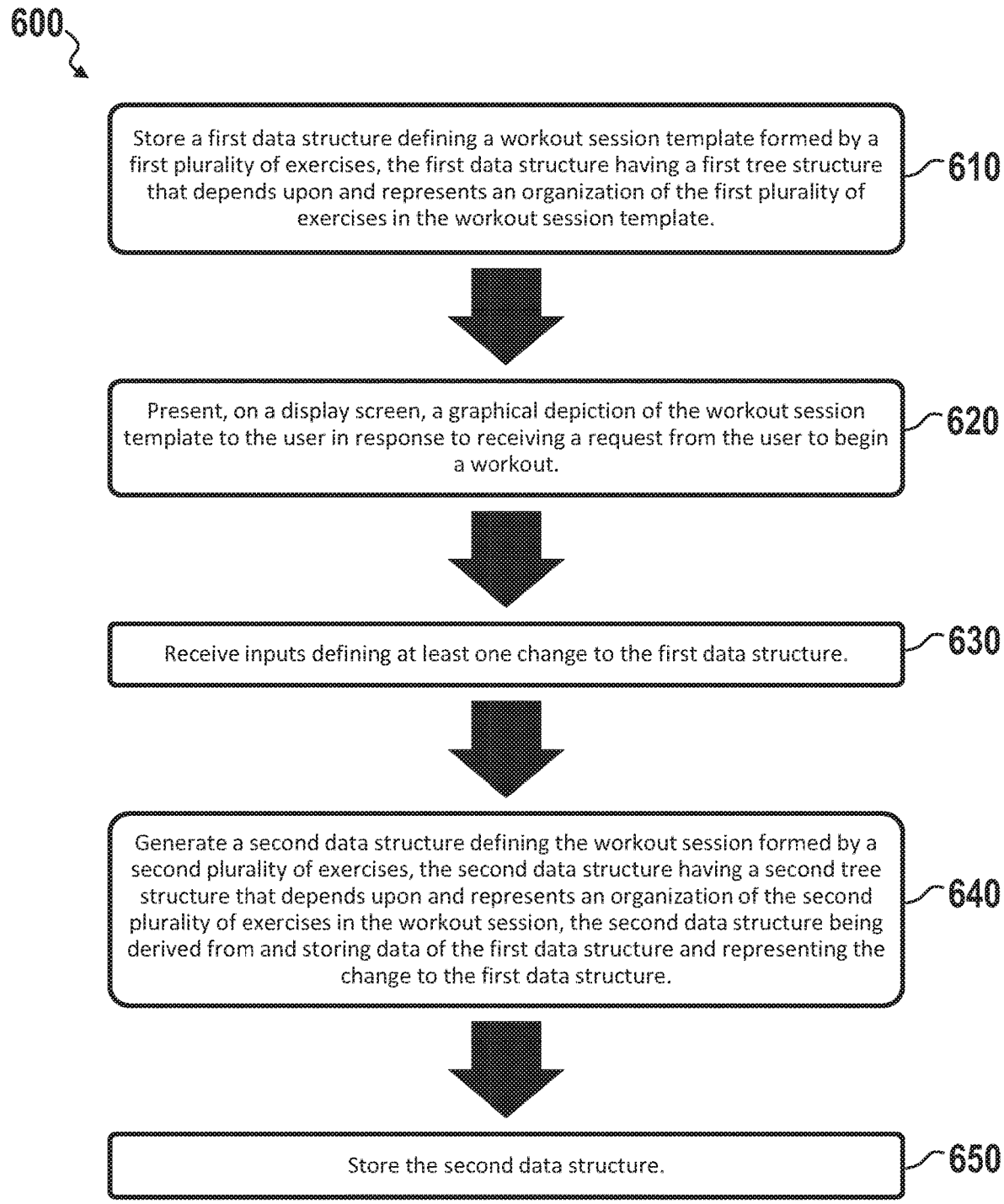
FIG. 8 shows a logical flow diagram for a method of collecting fitness data for a user during a workout session.

FIG. 8 shows a logical flow diagram for a method 600 of collecting fitness data for a user during a workout session. Particularly, the method 600 provides a method for collecting fitness data that advantageously utilizes the versatile data structure described above for representing a complex workout session template and also for storing fitness data relating to a particular workout session based on the complex workout session template. The method 600 improves upon the functioning of the fitness tracking system 10 and the devices thereof by enable a user to record fitness data associated with a complex workout session template with a minimal amount of user effort (i.e., with a minimum amount of button presses or other user interactions). Additionally, the method 600 improves upon the functioning of the fitness tracking system 10 and the devices thereof by providing a more robust collection a fitness data associated with complex workout session templates and enabling more advanced analysis and presentation of the fitness data. Finally, the advanced analysis enabled by the robust collection of fitness data can advantageously enable better coaching and guidance of the user, thereby improving user retention and real health outcomes for the users.

It should be appreciated that, although the method 600 is discussed below primarily with respect to the processor 37 of the personal electronic device 30, the processor 27 of the activity tracking device 20, which may be provided in the form of a so-called "smart" watch, may also execute instructions of a client-side activity tracking application to perform some or all of the steps of the method 600. Additionally, in some embodiments, the processor 47 of the system server 40 may execute instructions of a network-side activity tracking application to perform certain steps of the method 600.

The method 600 begins with a step of storing a first data structure defining a workout session template formed by a first plurality of exercises, the first data structure having a first tree structure that depends upon and represents an organization of the first plurality of exercises in the workout session template (block 610). Particularly, with respect to the embodiments described in detail herein, the memory 38 of the personal electronic device 30 is configured to store one or more workout session template data structures locally in the memory 38. Alternatively or in addition, the memory 48 of the system server 40 is configured to store one or more workout session template data structures locally in the memory 48. In some embodiments, the processor 47 of the system server is configured to operate the network communications module 49 to transmit one or more of the workout session template data structures to the personal electronic device 30. The processor 37 is configured to operate the transmitter/receiver 39 to receive the one or more of the workout session template data structures from the system server 40 and to store the one or more of the workout session template data structures in the memory 38. The workout session template data structures may have been generated using any of the techniques discussed above.

The method 600 continues with a step of presenting, on a display screen, a graphical depiction of the workout session template to the user in response to receiving a request from the user to begin a workout (block 620). Particularly, with respect to the embodiments described in detail herein, the processor 37 of the personal electronic device 30 is configured to execute instructions of the client-side activity tracking application to operate the I/O interface 36 to display a graphical user interface on the display screen 34 that includes a visual representation or graphical depiction of the workout session template in response to a request from the user to begin a workout session based on the workout session template. In at least one embodiment, the processor 37 of the personal electronic device 30 is configured to operate the I/O interface 36 to display a graphical user interface on the display screen 34 that includes a list of workout session templates defined in a plurality of workout session template data structures stored in the memory 38 of the personal electronic device 30 or in the memory 48 at the system server 40. The processor 37 of the personal electronic device 30 is configured to display the visual representation of a respective workout session template in response to receiving a selection of the respective workout session template from the list of workout session templates.

In at least one embodiment, the visual representation of the workout session template includes a plurality of data fields, which are editable by the user. Each data field is associated with an exercise in the plurality of exercises that make up the workout session template and, in particular, corresponds to a particular performance metric for the associated exercise in the plurality of exercises. In at least one embodiment, the data fields are visually organized according to the organization of the plurality of exercises in the workout session template.

In at least one embodiment, some or all of the data fields are automatically filled based on the target values for the respective performance metrics that are stored in the workout session template data structure. Alternatively, some or all of the data fields are automatically filled with suggested target values for the respective performance metrics. In one embodiment, the processor 37 is configured to calculate the suggested target values as a function of the target values that are stored in the workout session template data structure and/or as a function of fitness data relating to previous workout sessions. In particular, in the case that the target values are relative values, as discussed above (e.g., "Heavy" or "Fast"), the processor 37 may be configured to calculate a suggest value based on the relative target value and fitness data relating to previous workout sessions.

Figure 9A:
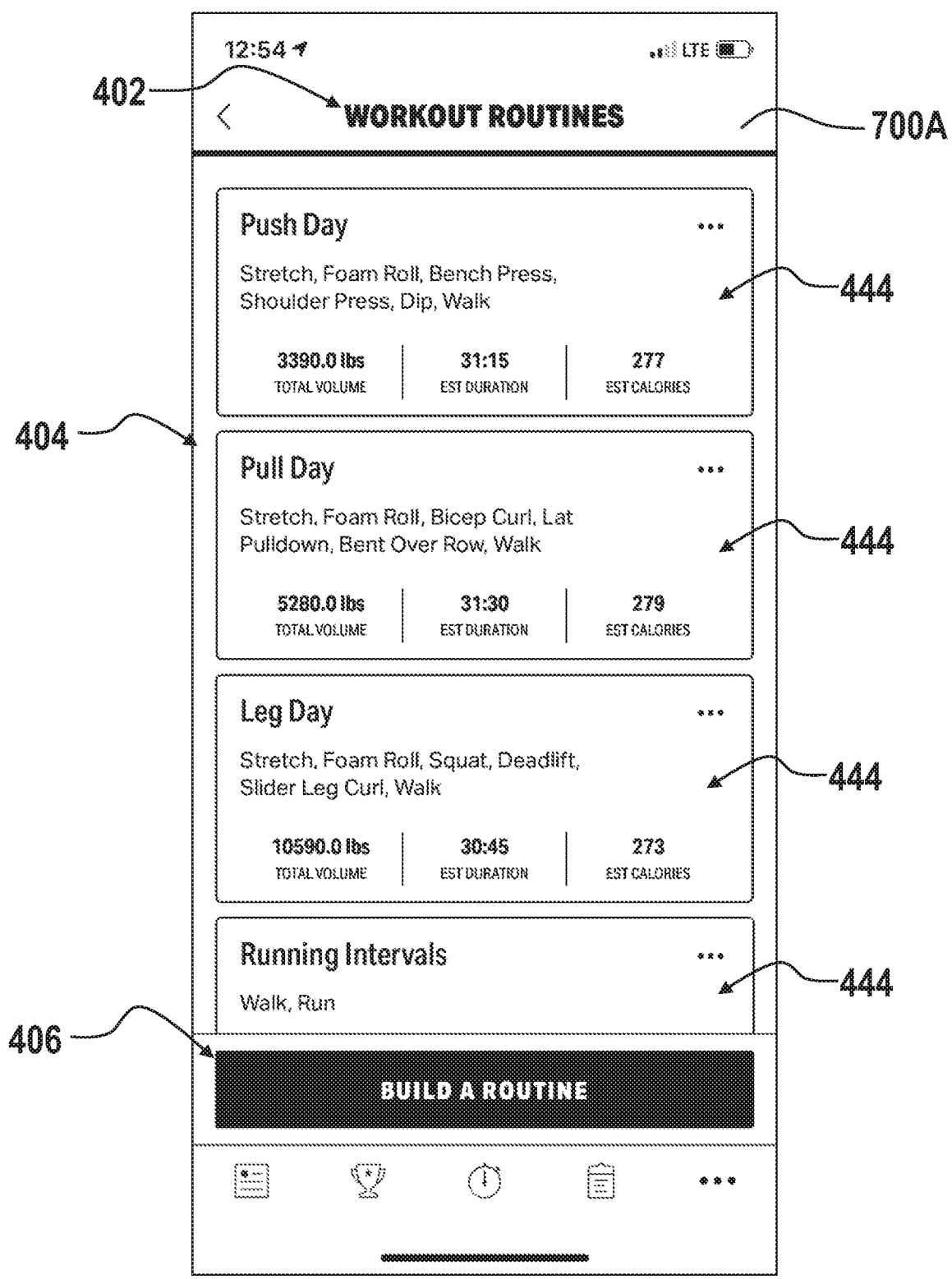
FIG. 9A-C show exemplary graphical user interfaces for recording performance metrics during a workout session.

FIG. 9A shows an exemplary embodiment of a workout session template selection screen 700A displayed on the display screen 34 of the personal electronic device 30. It will be appreciated, however, that an analogous workout session template selection screen can be displayed on the activity tracking device 20. The workout session template selection screen 700A is essentially similar to the workout session template selection screen 400A of FIG. 6A and includes the title 402, the workout session template selection region 404, and the workout session template creation option 406. However, in the workout session template selection screen 700A, the workout session template selection region 404 is no longer empty because the user has now designed or otherwise collected several workout session templates (e.g., "Push Day," "Pull Day," "Leg Day," and "Running Intervals"). Instead, the workout session template selection region 404 list of several workout session template options 444. In response to the user pressing or otherwise selecting one of the workout session template options 444, the processor 37 is configured to operate the I/O interface 36 to display a workout session screen on the display screen 34.

Figure 9B:
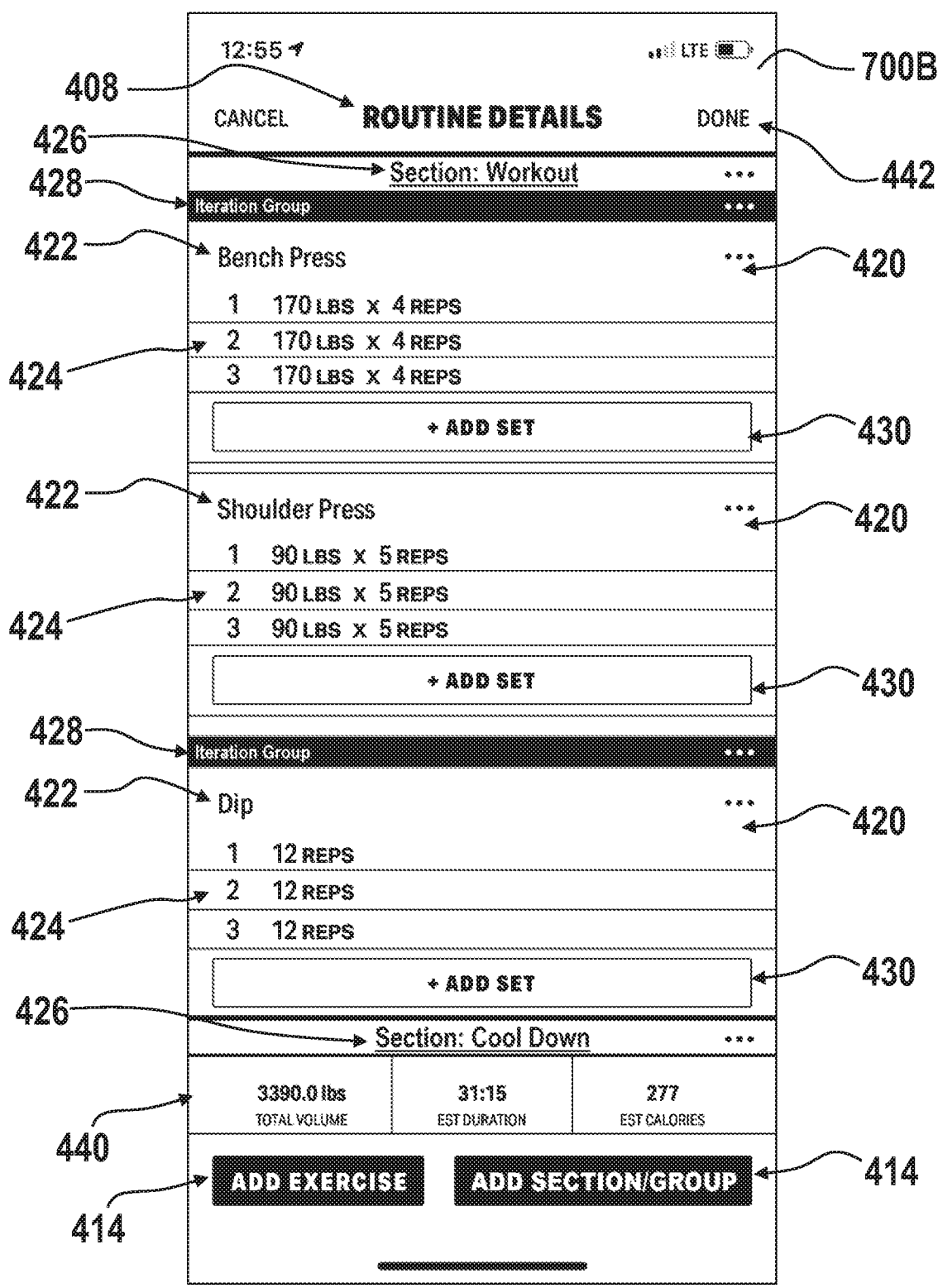

FIG. 9B shows an exemplary workout session screen 700B displayed on the display screen 34 of the personal electronic device 30. It will be appreciated, however, that an analogous workout session screen can be displayed on the activity tracking device 20. The workout session screen 700B is essentially similar to the workout session template creation screens 400B and 400C and included the title 408, the name field, the add exercise option 414, and the add section/group option 416. Additionally, the workout session screen 700B includes a visual representation of the workout session template in the form of the exercise segments 420 and group labels 426, 428. As with the workout session template creation screen 400C, the exercise segments 420 each include the exercise name label 422, the performance metric fields 424, and the add set option 430. However, as compared to the workout session template creation screen 400C, iteration groups are expanded in the workout session screen 700B such that the performance metric fields 424 include individual fields for each particular set that is performed. In this way, the user can record unique performance metric data for each individual set in the manner discussed above with respect to the exercise editing screen 400D. Finally, the workout session screen 700B includes the workout performance section 440, which may be updated dynamically as the user enters data into the performance metric fields 424.

The method 600 continues with a step of receiving user inputs defining at least one change to the first data structure (block 630). Particularly, with respect to the embodiments described in detail herein, the processor 37 of the personal electronic device 30 is configured to execute instructions of the client-side activity tracking application to receive operate the PO interface 36 and/or the transmitter/receiver 39 to receive a plurality of inputs from a user that one or more define at least one changed to the workout session template data structure. The change may comprise one or more of (i) adding actual values for performance metrics for exercises that form the workout session template (which may include values for which there are no target values), (ii) changes to the particular set of exercises that form the workout session template, or (iii) changes to the organization of the exercises in the workout session template, such as a change in the grouping or organization of the exercises. Additionally, the change may comprise merely adding metadata to identifying that the workout session was performed at particular time, including no additional changes to the workout session template.

In at least one embodiment, the processor 37 of the personal electronic device 30 is configured to execute instructions of the client-side activity tracking application to operate the I/O interface 36 to display a graphical user interface on the display screen 34, such as the workout session screen 700B. The user provides the plurality of inputs by interacting with the graphical user interface by, in the case of a touch screen 34, touching, tapping, swiping, or the like on the screen 34, or by operating some other user interface to interact with the graphical user interface.

In particular, with respect to the workout session screen 700B, in response to the user pressing or otherwise selecting the add exercise option 414, the processor 37 is configured to operate the I/O interface 36 to display one or more menus (not shown) to enable the user to search for and/or select an exercise to be added to the workout session template. Similarly, in response to the user pressing or otherwise selecting the add section/group option 416, the processor 37 is configured to operate the I/O interface 36 to display one or more menus (not shown) to enable the user to define one or more sections of the workout session and/or groups of exercises within the workout session. Finally, in response to the user pressing or otherwise selecting the performance metric fields 424, the processor 37 is configured to operate the I/O interface 36 to display an exercise editing screen on the display screen 34, via which the user can edit performance metric fields as described above with respect to the exercise editing screen 400D.

Finally, when the user has finished with the workout session and has recorded all the performance data he or she wishes to record, the user can press the done option 442 to log the workout session. Particularly, in response to the user pressing or otherwise selecting the done option 442, the processor 37 is configured to operate the I/O interface 36 to display a log workout screen on the display screen 34.

Figure 9C:
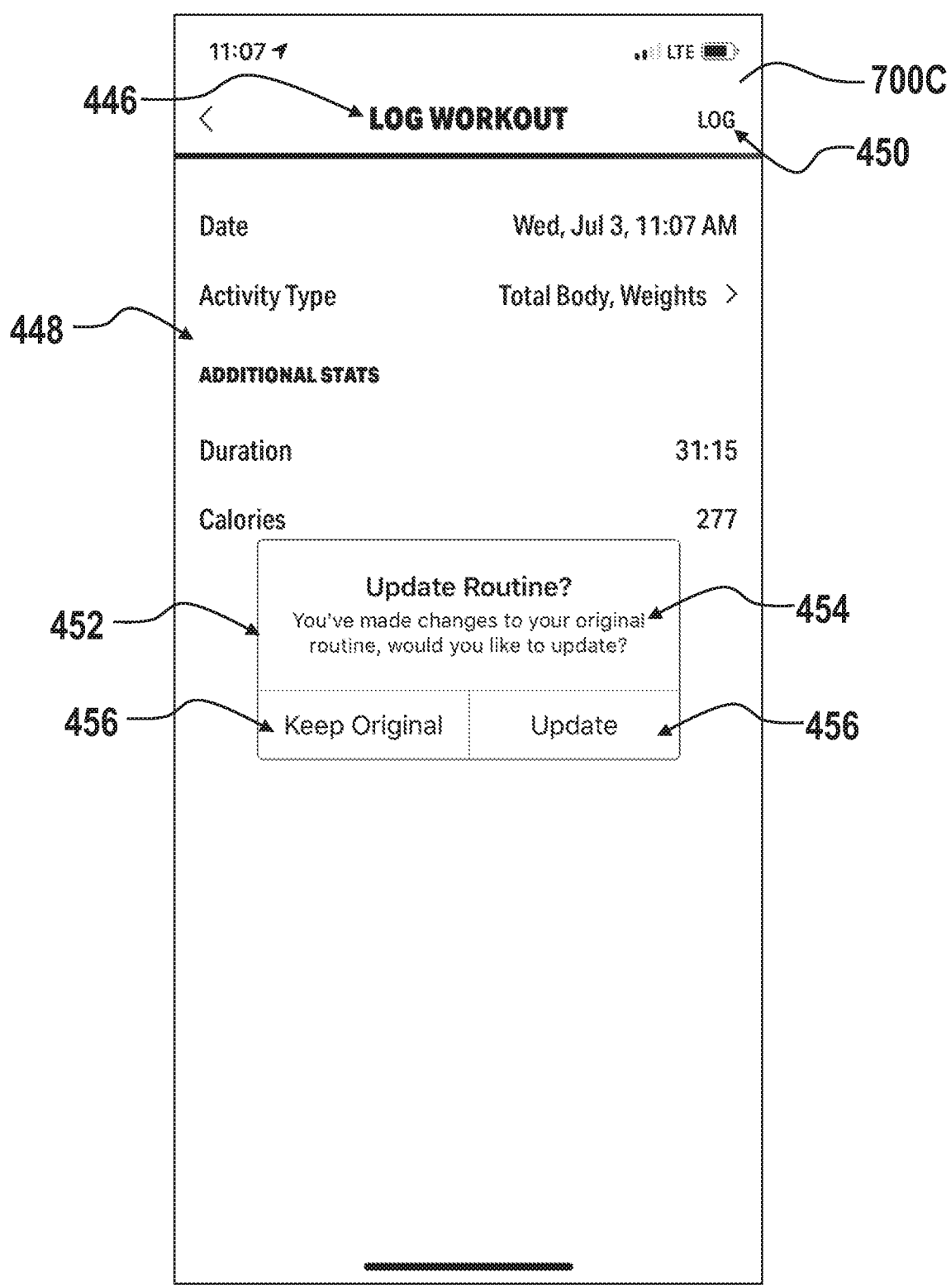

FIG. 9C shows a log workout screen 700C displayed on the display screen 34 of the personal electronic device 30. It will be appreciated, however, that an analogous log workout screen can be displayed on the activity tracking device 20. The log workout screen 700C includes a title 446 (e.g., "Log Workout") and a stats section 448 include a summary of one or more performance metrics and other data for the workout session. Finally, when the user has confirmed that he or she would like to record the workout session, the user can press the log option 450 to log the workout session.

In some embodiments, in response to any changes or edits being made in the data fields, any changes to the particular set of exercises that form the workout session template, or any changes to the organization of the exercises in the workout session template, the processor 37 is configured to operate the I/O interface 36 to display a prompt having selectable options, asking the user if he or she would like to update the workout session template with the changes that were made during the workout session. As used herein with respect to a data fields the term "change" or "edit" includes adding data to an empty data field or modifying data in an automatically filled data field. Particularly, the log workout screen 700C includes a prompt 452 having text 454 (e.g., "Update Routine? You've made changes to your original routine, would you like to update?") and selectable options 456 (e.g., "Keep Original" and "Update"). In response the user selecting the "Update" option, the processor 37 is configured to update the workout session template data structure to include the changes that were made to the workout session template during the workout session, i.e., to include updated target values for performance metrics, to add/remove segment template nodes, or to add/remove/adjust group template nodes.

The method 600 continues with a step of generating a second data structure defining the workout session formed by a second plurality of exercises, the second data structure having a second tree structure that depends upon and represents an organization of the second plurality of exercises in the workout session, the second data structure being derived from and storing data of the first data structure and representing the change to the first data structure (block 640). Particularly, with respect to the embodiments described in detail herein, the processor 37 of the personal electronic device 30 is configured to execute instructions of the client-side activity tracking application to generate a workout session data structure that defines a workout session based on the plurality of inputs received from the user and based on the workout session template data structure. The processor 37 is configured to generate the workout session data structure in the form discussed above having a tree structure that represents the organization of the exercises in the workout session. In order to generate the workout session data structure, the processor 37 is configured to convert each node of the workout session template data structure to its workout session counterpart. Particularly, the processor 37 is configured to derive the workout session data structure based on the workout session template data structure by converting each segment template node to a segment node, converting each group template node to a group node, converting each segment group template node to a segment group node, and converting each iteration group template node to an iteration group node.

As described above, the nodes of the workout session data structure store actual values for performance metrics for exercises of the workout session and target values for performance metrics for exercises of the workout session template. The target values stored in the workout session data structure are retrieved from the workout session template data structure as it existed prior to the workout session (i.e., before any updates/changes were made during the workout session). The workout session data structure also represents any structural and/or organizational changes compared to workout session template data structure. The workout session data structure is adapted to reflect these changes, as well as store information regarding the original intended organization of the corresponding workout session template as it existed prior to the workout session. In this way, regardless of any updates to or even an eventual deletion of the workout session template, information regarding the intended workout session template with the original target values for the performance metrics are advantageously stored with the workout session data structure.

In some embodiments, the segments may include data indicating start and end times for the respective exercise, which may have been input manually by the user or automatically detected. The start and end times can be manually entered by the user, automatically detected based on sensor data, or some combination thereof. In one embodiment, the processor 37 is configured to retrieve a subset of fitness data recorded by a sensor of the activity tracking device or personal electronic device based on start and end times for a respective exercise. The retrieved subset of fitness data can be stored, or otherwise associated with the segment node in the segment node for the exercise.

The method 600 continues with a step of storing the second data structure (block 650). Particularly, with respect to the embodiments described in detail herein, the processor 37 of the personal electronic device 30 is configured to execute instructions of the client-side activity tracking application to store the workout session data structure for the workout session in a memory. In this way, regardless of any updates to or even an eventual deletion of the workout session template, information regarding the intended workout session template with the original target values for the performance metrics are advantageously stored with the workout session data structure. In one embodiment, the workout session data structure is stored in a database, which may be the same as or distinct from a database that stores workout session template data structures. In one embodiment, the processor 37 is configured to store the workout session data structure locally in the memory 38. Alternatively or in addition, in some embodiments, the processor 37 is configured to operate the transmitter/receiver 39 to transmit the workout session data structure to the system server 40. The processor 47 of the system server is configured to operate the network communications module 49 to receive the workout session data structure, and to store the workout session data structure in the memory 48.

In some embodiments, the detailed fitness data recorded utilizing the versatile data structure described herein can be used for robust analysis and coaching features. Particularly, in one embodiment, detailed performance summaries, comparisons and trends can be determined and displayed to the user based on the fitness data stored in the workout session data structures. Additionally, in one embodiment, suggestions can be made to the user based on the fitness data with respect to how the user can improve his or her fitness performance and health outcomes.

In another embodiment, a permanent copy of the programming instructions for individual ones of the aforementioned applications (e.g., the client-side activity tracking application and/or the server-side activity tracking application) may be placed into permanent storage devices (such as e.g., the memories 28, 38, 48) during manufacture thereof, or in the field, through e.g., a distribution medium (not shown), such as a compact disc (CD), or through communication devices 29, 39, 49 (from a distribution server). That is, one or more distribution media having an implementation of the agent program may be employed to distribute the agent and program various computing devices.

The herein described applications (e.g., the client-side activity tracking application and/or the server-side activity tracking application) improve the functioning of the activity tracking device 20, the personal electronic device 30 and/or system server 40, respectively or in combination by enabling it/them to provide robust collection a fitness data associated with complex workout session templates, with a minimal amount of user effort (i.e., with a minimum amount of button presses or other user interactions). Particularly, the versatile data structure utilized by the fitness tracking system 10 enables robust representation of many popular fitness activities, such as strength training, circuit training, and interval training, which are poorly suited for conventional fitness tracking systems that are designed primarily for fitness activities that are continuously performed for a period of time. Furthermore, devices that are able to record fitness data in a robust manner can operate more efficiently to provide more advanced analysis and presentation of the fitness data. Finally, the advanced analysis enabled by the robust collection of fitness data can advantageously enable better coaching and guidance of the user, thereby improving user retention and real health outcomes for the users.

The foregoing detailed description of one or more exemplary embodiments of the fitness tracking system 10 has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

What is claimed is:

1. A method of collecting fitness data for a user during a workout session, the method comprising:
   storing, in a memory, a first data structure defining a workout session template formed by a first plurality of exercises, the first data structure having a first tree structure that depends upon and represents an organization of the first plurality of exercises in the workout session template;
   presenting, with a display screen, a graphical depiction of the workout session template to the user in response to receiving a request from the user to begin a workout;
   receiving, with a user interface, first inputs defining at least one change to the first data structure;

generating, with the processor, a second data structure defining the workout session formed by a second plurality of exercises, the second data structure having a second tree structure that depends upon and represents an organization of the second plurality of exercises in the workout session, the second data structure being derived from and storing data of the first data structure and representing the change to the first data structure; and storing, in the memory, the second data structure.

2. The method according to claim 1, wherein the at least one change to the first data structure includes at least one of (i) an actual value for at least one performance metric for at least one exercise in the first plurality of exercises, (ii) a change to the exercises in the first plurality of exercises, and (iii) a change to the organization of the first plurality of exercises in the workout session template.

3. The method according to claim 1, wherein:

the first tree structure of the first data structure has a plurality of segment template nodes corresponding to the first plurality of exercises and a plurality of group template nodes corresponding a plurality of groups in the organization of the first plurality of exercises in the workout session template, the first tree structure defining each segment template node in the plurality of segment template nodes as childless, the first tree structure defining each group template node in the plurality of group template nodes as having at least one child including at least one of (i) a segment template node from the plurality of segment template nodes and (ii) a further group template node from the plurality of group template nodes; and the second tree structure of the second data structure has a plurality of segment nodes corresponding to the second plurality of exercises and a plurality of group nodes corresponding a plurality of groups in the organization of the second plurality of exercises in the workout session, the second tree structure defining each segment node in the plurality of segment nodes as childless, the second tree structure defining each group node in the plurality of group nodes as having at least one child including at least one of (i) a segment node from the plurality of segment nodes and (ii) a further group node from the plurality of group nodes.

4. The method according to claim 3, wherein:

the plurality of group template nodes of the first tree structure includes at least one iteration group template node defining an iteration group in the organization of the first plurality of exercises in the workout session template, which defines a number of iterations to be performed for exercises within the respective iteration group; and the plurality of group nodes of the second tree structure includes at least one iteration group node defining an iteration group in the organization of the second plurality of exercises in the workout session, which defines a number of iterations that were performed for exercises within the respective iteration group.

5. The method according to claim 3, wherein:

a segment template node in the plurality of segment template nodes, corresponding to a first exercise, stores a target value for a performance metric for the first exercise; and a segment node in the plurality of segment nodes, corresponding to the first exercise, stores (i) an actual value for the performance metric for the first exercise and (ii) the target value for the performance metric for the first exercise.

6. The method according to claim 1, further comprising:

receiving, prior to the workout, with the user interface, second inputs from a user that define the first plurality of exercises that form the workout session template and the organization of the first plurality of exercises in the workout session template;

generating, prior to the workout, with the processor, the first data structure defining the workout session template based on the second inputs.

7. The method according to claim 1, further comprising:

extracting the first plurality of exercises that form the workout session template and the organization of the first plurality of exercises in the workout session template from one of (i) a body of text, and (ii) fitness data recording during a previous workout; and generating, prior to the workout, with the processor, the first data structure defining the workout session template based on the extracted first plurality of exercises and the extracted organization of the first plurality of exercises.

8. The method according to claim 1, further comprising:

receiving, prior to the workout, with a receiver, the first data structure from a remote server, the first data structure having been generated by another user.

9. The method according to claim 1, the presenting the workout session template further comprising:

displaying, with the display screen, a plurality of user-editable data fields associated with each exercise in the first plurality of exercises, the plurality of data fields being visually organized according to the organization of the first plurality of exercises in the workout session template, each data field in the plurality of data fields corresponding to a particular performance metric for the associated exercise in the first plurality of exercises, wherein at least some of the first inputs include data entered into the plurality of data fields by the user.

10. The method according to claim 9, the presenting the workout session template further comprising:

automatically filling at least one data field in the plurality of data fields with a respective target value that is stored in the first data structure for the corresponding performance metric for the associated exercise.

11. The method according to claim 9, further comprising:

displaying, with the display screen, a prompt having options that are selectable by the user, in response to receiving the first inputs defining an actual value for at least one performance metric for at least one exercise in the first plurality of exercises; and storing, in response to the user selecting a first option from the prompt, the actual value in the first data structure as a target value the at least one performance metric for the at least one exercise.

12. The method according to claim 1, the receiving second inputs further comprising:

displaying, with the display screen, a prompt having options that are selectable by the user, in response to receiving the first inputs defining the change to the first tree structure; and updating, in response to the user selecting a first option from the prompt, the first tree structure of the first data structure based on the first inputs defining the change to the first tree structure.

13. The method according the claim 1, further comprising:
- receiving fitness data from a sensor configured to measure the fitness data with respect to the user during the workout session;
- receiving the first inputs defining a start time and an end time for performance at least one exercise in the plurality of exercises by the user; and
- at least one of associating and storing a subset of the fitness data from the sensor with the second data structure based on the start time and the end time.

14. A method of collecting fitness data for a user during a workout session, the method comprising:
- storing, in a memory, a plurality of first data structures each defining a respective workout session template formed by a respective first plurality of exercises, each data structure in the plurality of first data structures having a respective first tree structure that depends upon and represents an organization of the respective first plurality of exercises in the respective workout session template;
- presenting, with a display screen, a list of the respective workout session templates defined in the plurality of first data structures;
- presenting, with a display screen, a graphical depiction of a first workout session template to the user in response to receiving a selection of the first workout session template from the list of templates;
- receiving, with a user interface, inputs defining an actual value for at least one performance metric for at least one exercise in the respective first plurality of exercises that form the first workout session template;
- generating, with the processor, a second data structure defining the workout session formed by a second plurality of exercises, the second data structure having a second tree structure that depends upon and represents an organization of the second plurality of exercises in the workout session, the second data structure being derived from and storing data of the respective first data structure that defines the first workout session template, the second tree structure storing the actual value for the at least one performance metric for the at least one exercise; and
- storing, in the memory, the second data structure.

15. The method according to claim 14, wherein:
- for each first data structure in the plurality of first data structures, the respective first tree structure has a plurality of segment template nodes corresponding to the first plurality of exercises and a plurality of group template nodes corresponding a plurality of groups in the organization of the first plurality of exercises in the workout session template, the respective first tree structure defining each segment template node in the plurality of segment template nodes as childless, the respective first tree structure defining each group template node in the plurality of group template nodes as having at least one child including at least one of (i) a segment template node from the plurality of segment template nodes and (ii) a further group template node from the plurality of group template nodes; and
- the second tree structure of the second data structure has a plurality of segment nodes corresponding to the second plurality of exercises and a plurality of group nodes corresponding a plurality of groups in the organization of the second plurality of exercises in the workout session, the second tree structure defining each segment node in the plurality of segment nodes as childless, the second tree structure defining each group node in the plurality of group nodes as having at least one child including at least one of (i) a segment node from the plurality of segment nodes and (ii) a further group node from the plurality of group nodes.

16. The method according to claim 14, further comprising:
- receiving, prior to the workout, with the user interface, second inputs from a user that define a plurality of exercises that form a respective workout session template and the organization of the plurality of exercises in the respective workout session template;
- generating, prior to the workout, with the processor, one of the first data structures in the plurality of first data structures based on the second inputs.

17. The method according to claim 14, further comprising:
- extracting a plurality of exercises that form a respective workout session template and an organization of the plurality of exercises in the respective workout session template from one of (i) a body of text, and (ii) fitness data recording during a previous workout; and
- generating, prior to the workout, with the processor, one of the first data structures in the plurality of first data structures based on the extracted plurality of exercises and the extracted organization of the plurality of exercises.

18. The method according to claim 14, the presenting the first workout session template further comprising:
- displaying, with the display screen, a plurality of user-editable data fields associated with each exercise in the respective first plurality of exercises that form the first workout session template, the plurality of data fields being visually organized according to the organization of the respective first plurality of exercises in the first workout session template, each data field in the plurality of data fields corresponding to a particular performance metric for the associated exercise in the respective first plurality of exercises,
- wherein at least some of the first inputs include data entered into the plurality of data fields by the user.

19. The method according to claim 18, further comprising:
- displaying, with the display screen, a prompt having options that are selectable by the user, in response to receiving the first inputs defining the actual value for the at least one performance metric for the at least one exercise; and
- storing, in response to the user selecting a first option from the prompt, the actual value in the first data structure as a target value for the at least one performance metric for the at least one exercise.

20. An electronic device for collecting fitness data for a user during a workout session comprising:
- a display screen configured to display a graphical user interface to a user;
- a user interface configured to receive inputs from the user;
- a memory configured to store a first data structure defining a workout session template formed by a first plurality of exercises, the first data structure having a first tree structure that depends upon and represents an organization of the first plurality of exercises in the workout session template; and
- a processor operably connected to the display screen, the user interface, and the memory, the processor configured to execute program instructions to:

operate the display screen to present a graphical depiction of the workout session template to the user in response to receiving a request from the user to begin a workout;

operate the user interface to receive first inputs defining at least one change to the first data structure, the at least one change to the first data structure including at least one of (i) an actual value for at least one performance metric for at least one exercise in the first plurality of exercises, (ii) a change to the exercises in the first plurality of exercises, and (iii) a change to the organization of the first plurality of exercises in the workout session template;

generate a second data structure defining the workout session formed by a second plurality of exercises, the second data structure having a second tree structure that depends upon and represents an organization of the second plurality of exercises in the workout session, the second data structure being derived from and storing data of the first data structure and representing the change to the first data structure; and operate the memory store the second data structure.

\* \* \* \* \*